US012775852B2

(12) United States Patent
Milenkovic et al.

(10) Patent No.: US 12,775,852 B2
(45) Date of Patent: Oct. 27, 2026

(54) ON-CHIP NANOSCALE STORAGE SYSTEM USING CHIMERIC DNA

(71) Applicant: The Board of Trustees of the University of Illinois, Urbana, IL (US)

(72) Inventors: Olgica Milenkovic, Urbana, IL (US); Nagendra Athreya, Urbana, IL (US); Apratim Khandelwal, Champaign, IL (US); Jean-Pierre Leburton, Urbana, IL (US); Xiuling Li, Champaign, IL (US); Charles Schroeder, Champaign, IL (US); Seyedkasra Tabatabaei, Urbana, IL (US); Bo Li, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 553 days.

(21) Appl. No.: 18/355,107

(22) Filed: Jul. 19, 2023

(65) Prior Publication Data

US 2024/0046114 A1 Feb. 8, 2024

Related U.S. Application Data

(63) Continuation of application No. 16/593,450, filed on Oct. 4, 2019, now Pat. No. 11,755,922.

(51) Int. Cl.
*G06N 3/123* (2023.01)
*C12N 7/00* (2006.01)

(52) U.S. Cl.
CPC ............... *G06N 3/123* (2013.01); *C12N 7/00* (2013.01); *C12N 2310/3181* (2013.01);
(Continued)

(58) Field of Classification Search
CPC .......... G06N 3/123; G06N 20/00; C12N 7/00; C12N 2310/3181; C12N 2310/52;
(Continued)

(56) References Cited

U.S. PATENT DOCUMENTS 8,192,600 B2 6/2012 Leburton et al.
8,702,929 B2 4/2014 Leburton et al.
(Continued)

FOREIGN PATENT DOCUMENTS

WO 2014/171969 10/2014

OTHER PUBLICATIONS

Richard P. Feynman, "There's Plenty of Room at the Bottom", Engineering and Science, Feb. 1960, pp. 22-36.
(Continued)

*Primary Examiner* — Jason W Blust
(74) *Attorney, Agent, or Firm* — McDonnell Boehnen Hulbert & Berghoff LLP

(57) ABSTRACT

The present disclosure provides systems and methods that can provide portable, real-time accessible DNA memories. An example DNA-based data storage system includes a loading region configured to receive a plurality of DNA-based data storage elements in a suspension fluid and a plurality of microtubes disposed in a capture/release region. The microtubes are configured to capture and release the DNA-based data storage elements. The DNA-based data storage system also includes a linearization region configured to linearize the DNA-based data storage elements and a readout region with a readout device configured to provide information indicative of the respective DNA-based data storage elements.

7 Claims, 17 Drawing Sheets

Specification includes a Sequence Listing.

(52) U.S. Cl.
CPC .................... *C12N 2310/52* (2013.01); *C12N 2795/00031* (2013.01); *C12N 2795/00042* (2013.01)

(58) Field of Classification Search
CPC ........... C12N 2795/00031; C12N 2795/00042; C12N 2795/14131; C12N 2795/14142; C40B 40/06
See application file for complete search history.

(56) References Cited

U.S. PATENT DOCUMENTS

| | | | |
|---|---|---|---|
| 8,941,460 B2 | 1/2015 | Li et al. | |
| 9,018,050 B2 | 4/2015 | Li et al. | |
| 9,224,532 B2 | 12/2015 | Li et al. | |
| 9,330,829 B2 | 5/2016 | Li et al. | |
| 10,003,317 B2 | 6/2018 | Li et al. | |
| 10,276,942 B2 | 4/2019 | Li et al. | |
| 10,345,289 B2 | 7/2019 | Leburton | |
| 10,677,752 B2 | 6/2020 | Leburton | |
| 11,515,012 B1* | 11/2022 | Arnold | G06F 12/0646 |
| 2009/0035777 A1 | 2/2009 | Kokoris et al. | |
| 2009/0118140 A1 | 5/2009 | Suzara | |
| 2009/0124571 A1 | 5/2009 | Morvan et al. | |
| 2010/0291485 A1 | 11/2010 | Lapsys et al. | |
| 2010/0298530 A1 | 11/2010 | Fujimoto et al. | |
| 2016/0159834 A1 | 6/2016 | Lee et al. | |
| 2017/0002355 A1 | 1/2017 | Appella et al. | |
| 2017/0074855 A1 | 3/2017 | Morin et al. | |
| 2018/0075956 A1 | 3/2018 | Li et al. | |
| 2018/0101487 A1* | 4/2018 | Peck | C07H 21/04 |
| 2019/0244109 A1* | 8/2019 | Bramlett | G06F 17/40 |
| 2021/0141568 A1* | 5/2021 | Anavy | G06F 3/0659 |
| 2021/0210171 A1* | 7/2021 | Stirparo | G06F 11/1076 |

OTHER PUBLICATIONS

Enghiad and Zhao, "Programmable DNA-Guided Artificial Restriction Enzymes", ACS Synth. Biol., 2017, 6, 752-757.
Errol C. Friedberg, "DNA damage and repair", Nature, vol. 421, Jan. 23, 2003, 436-440.
Feng et al., "Identification of single nucleotides in MoS2 nanopores", Nature nanotechnology 10.12, 1070-1076.
Foloppe and Mackerell, Jr., "All-Atom Empirical Force Field for Nucleic Acids: I. Parameter Optimization Based on Small Molecule and Condensed Phase Macromolecular Target Data", Journal of Computational Chemistry, vol. 21, No. 2, 86-104 (2000).
Chun et al., "Geometry Effect on the Strain-Induced Self-Rolling of Semiconductor Membranes", Nano Lett., 2010, 3927-3932.
Erlich and Zielinski, "DNA Fountain enables a robust and efficient storage architecture", Science 355, 950-954 (2017) 4 pages.
Cisco Visual Networking, "The Zettabyte Era: Trends and Analysis", May 2015, pp. 1-29.
Bulushev et al., "Single Molecule Localization and discrimination of DNA-Protein Complexes by Controlled Translocation Through Nanocapillaries", Nano Lett, 2016, 16, 7882-7890.
Densmore and Bhatia, "Bio-design automation: software + biology + robots", Trends in Biotechnology, Mar. 2014, vol. 32, No. 3, 111-113.
Braha et al., "Designed protein pores as components for biosensors", Chemistry & Biology, 1997, vol. 4, No. 7, 497-505.
Bryksin and Matsummura, "Overlap extension PCR cloning: a simple and reliable way to create recombinant plasmids", Bio Techniques 48:463-465, Jun. 2010.
Church et al., "Next-Generation Digital Information Storage in DNA", Science, vol. 337, Sep. 28, 2012, 1628.
Appleton et al., "Design Automation in Synthetic Biology", Cold Spring Harbor Perspectives in Biology, 2017, 9:a023978, pp. 1-28.
Capek et al., "An Efficient Method for the Construction of Functionalized DNA Bearing Amino Acid Groups through Cross-Coupling Reactions of Nucleoside Triphosphates Followed by Primer Extension or PCR", Chem. Eur. J., 2007, 13, 6196-6203.
Brundo and Liu, "Recent Progress Toward the Templated Synthesis and Directed Evolution of Sequence-Defined Synthetic Polymers", Chemistry & Biology, 16, Mar. 27, 2009, 265-276.
Kim et al., "Scaling the Aspect Ratio of Nanoscale closely Packed Silicon Vias by MacEtch: Kinetics of Carrier Generation and Mass Transport", Adv. Funct. Mater., 2017, 27, 1605614, 8 pages.
Brownie et al., "The elimination of primer-dimer accumulation in PCR", Nucleic Acids research, 1997, vol. 25, No. 16, 3235-3241.
Brockman et al., "Direct observation of single flexible polymers using single stranded DNA", Soft Matter, 2011, 7, 8005-8012.
Bornholt et al., "A DNA-Based Archival Storage System", Proceeding of the Twenty-First International Conference on Architectural Support for Programming Languages and Operating Systems, 2016, 13 pages.
Leonard M. Adleman, "Computing with DNA—The manipulation of DNA to solve mathematical problems is redefining what is meant by computation", Scientific American, vol. 279, No. 2, Aug. 1998, 54-61.
Aksimentiev et al., "Microscopic Kinetics of DNA Translocation through Synthetic Nanopores", Biophysical Journal, vol. 87, Sep. 2004, 2086-2097.
Batu et al., "Reconstructing Strings from Random Traces", Departmental Papers (CIS) 2004:173, pp. 910-918.
Abiko et al., "Development of Constant Altitude Flight System Using Two Dimensional Laser Range Finder with Mirrors," 2017 IEEE International Conference on Advanced Intelligent Mechatronics (AIM), Munich Germany, Jul. 3-7, 2017, 6 pages.
European Patent Office, Extended European Search Report mailed on Jul. 26, 2023, issued in connection with European Patent Application No. 20862998.0, 14 pages.
Noguchi et al., "Capturing Device for Dense Point Cloud of Indoor People using Horizontal LIDAR and Pan Rotation of Vertical LIDAR with Mirrors," 2012 IOEE/SICE International Symposium on System Integration (SII), Kyushu University, Fukuoka, Japan, Dec. 16-18, 2012, 6 pages.
Velodyne Lidar, "How to Change the Laser Angle and FoV on a Velodyne VLP-16," Oct. 25, 2016, 5 pages, retrieved from internet: https://velodynelidar.com/blog/how-to-change-the-laser-angle-and-fov-on-a-veloydne-vlp-16.
Lutz et al., "Sequence-Controlled Polymers", Science, 341, 1238149 (2013).
Li et al., "Progress in developing Poisson-Boltzmann equation solvers", Molecular Based Mathematical Biology, Research Article, 2013, 42-62.
MacKerell, Jr. et al., "All-Atom Empirical Potential for Molecular Modeling and Dynamics Studies of Proteins", J. Phys. Chem. B, 1998, 102, 3586-3616.
Li et al., "Modeling the stretching of wormlike chains in the presence of excluded volume", Soft Matter, 2015, 11, 5947-5954.
Loman and Watson, "Successful test launch for nanopore sequencing", Nature Methods, vol. 12, No. 4, Apr. 2015, 303-304.
Xiuling Li, "Metal assisted chemical etching for high aspect ratio nanostructures: A review of characteristics and applications in photovoltaics", Current Opinion in Solid State and Materials Science 16 (2012) 71-81.
Li et al., "When Ends Meets: Circular DNA Stretches Differently in Elongational Flows", Macromolecules, 2015, 48, 5997-6001.
Xiuling Li, "Self-rolled-up microtube ring resonators: a review of geometrical and resonant properties", Advances in Optics and Photonics, 3, 366-387 (2011).
Yu et al., "Ultra-Small, High-Frequency, and Substrate-Immune Microtube Inductors Transformed from 2D to 3D", Scientific Reports, 5:9661, Apr. 27, 2015, pp. 1-6.
Latinwo et al., "Nonequilibrium thermodynamics of dilute polymer solutions in flow", J. Chem. Phys. 141, 174903 (2014) 10 pages.
Huang et al., "Precision Structural Engineering of Self-Rolled-up 3D Nanomembranes Guided by transient Quasi-Static FEM Modeling", Nano Letters, 2014, 14, 6293-6297.
Hsiao et al., "Direct observation of DNA dynamics in semidilute solutions in extensional flow", J. Rheol. 61(1), 151-167, Jan./Feb. 2017, 151-167.

(56) References Cited

OTHER PUBLICATIONS

Liu et al., "Crystalline Two-Dimensional DNA-Origami Arrays", Angew. Chem, 2011, 123, 278-281.
Li et al., "Synthesis of many different types of organic small molecules using one automated process", Science Research Reports, vol. 347, Mar. 13, 2015, 1221-1226.
Laure et al., "Coding in 2D: Using Intentional Dispersity to Enhance the Information Capacity of Sequence-Coded Polymer Barcodes", Angew. Chem., 2016, 128, 10880-10883.
Latinwo et al., "Nonequilibrium Wrok Relations for Polymer Dynamics in Dilute Solutions", Macromolecules, 2013, 46, 8345-8355.
Kosuri and Church, "Large-scale de novo DNA synthesis: technologies and applications", Nature Methods, vol. 11, No. 5, May 2014, 499-507.
Eric T. Kool, "Replacing the Nucleobases in DNA with Designer Molecules", Acc. Chem. Res., 2002, 35, 936-943.
Jang et al., "Vertical Cell Array using TCAT(Terabit Cell Array Transistor) Technology for Ultra High Density NAND Flash Memory", 2009 Symposium on VLSI Technology Digest of Technical Papers, 192-193.
Klove et al., "Some Codes Correcting Asymmetric Errors of Limited Magnitude", IEEE Transactions on Information Theory, vol. 57, No. 11, Nov. 2011, 7459-7472.
Kiah et al., "Codes for DNA Sequence Profiles", Feb. 2, 2015, 27 pages.
Kiick et al., "Expanding the Scope of Protein Biosynthesis by Altering the Methionyl-tRNA Synthetase Activity of a Bacterial Expression Host", Angew. Chem. Int. Ed., 2000, 39, No. 12, 2148-2152.
Johnson and Panousis, "The Influence of Debye Length on the C-V Measurement of Doping Profiles", IEEE Transactions on Electron Devices, vol. Ed-18, No. 10, Oct. 1971, 965-973.
Kiah et al., "Codes for DNA Storage Channels", Oct. 31, 2014, 5 pages.
Hsiao et al., "Ring Polymer Dynamics Are Governed by a Coupling between Architecture and Hydrodynamic Interactions", Macromolecules, 2016, 49, 1961-1971.
Humphrey et al., "VMD: Visual Molecular Dynamics", Journal of Molecular Graphics, 14:33-38, 1996.
Huang et al., "RFIC Transformer with 12X Size Reduction and 15X Performance Enhancement by Self-Rolled-Up Membrane Nanotechnology", Proceedings of the ASME 2015 International Technical Conference and Exhibition on Packaging and Integration of Electronic and Photonic Microsystems, InterPACK2015, Jul. 6-9, 2015, San Francisco, California, 4 pages.
Huang et al., "Self-rolled-up Tube Transformers: Extreme Miniaturization and Performance Enhancement", IEEE, 2015, 223-224.
Froeter et al., "3D hierarchical architectures based on self-rolled-up silicon nitride membranes", Nanotechnology 24 (2013) 9 pages.
Froeter et al., "Toward Intelligent Synthetic Neural Circuits: Directing and Accelerating Neuron Cell Growth by Self-Rolled-Up Silicon Nitride Microtube Array", ACSNANO, vol. 8, No. 11, 2014, 11108-11117.
Hossein et al., "Portable and Error-Free DNA-Based Data Storage", Scientific Reports, 7, 5011, Jul. 10, 2017, 1-6.
Holzberger and Marx, "Enzymatic synthesis of perfluoroalkylated DNA", Bioorganic & Medicinal Chemistry; 17 (2009) 3653-3658.
Grass et al., "Robust Chemical Preservation of Digital Information on DNA in Silica with Error-Correcting Codes", Angew. Chem. Int. Ed., 2015, 54, 2552-2555.
Michal Horovitz, "Reconstruction of Sequences over Non-Identical Channels", 2017 IEEE International Sumposium on Information Theory (ISIT), 1510-1514.
Heckel et al., "Fundamental Limits of DNA Storage Systems", May 12, 2017, 11 pages.
Prinz et al., "Free-standing and overgrown InGaAs/GaAs nanotubes, nanohelices and their arrays", Physica E 6 (2000) 828-831.
Gracheva et al., "Simulation of the electric response of DNA translocation through a semiconductor nanopore-capacitor", Nanotechnology 17 (2006) 622-633.
Guruswami and Sudan, "Improved Decoding of Reed-Solomon and Algebraic-Geometric Codes", Proceedings 39th Annual Symposium on Foundations of Computer Science (Cat. No. 98CB36280), IEEE, 1998, pp. 1-10.
Goldman et al., "Towards practical, high-capacity, low-maintenance information storage in synthesized DNA", Nature, vol. 494, Feb. 7, 2013, 77-80.
Gracheva et al., "Electrical signatures of single-stranded DNA with single base mutations in a nanopore capacitor", Nanotechnology 17 (2006) 3160-3165.
Girdhar et al., "Tunable graphene quantum point contact transistor for DNA detection and characterization", Nanotechnology 26 (2015) 10 pages.
Girdhar et al., "Graphene quantum point contact transistor for DNA sensing", PNAS, Oct. 15, 2013, vol. 110, No. 42, 16748-16753.
Gallagher et al., "Low-Density Parity-Check Codes", IRE Transactions on Information Theory, pp. 21-28.
Gabrys et al., "Asymmetric Lee Distance Codes for DNA-Based Storage", IEEE Transactions on Information Theory, vol. 63, No. 8, Aug. 2017, 4982-4995.
Gabrys et al., "Codes in the Damerau Distance for DNA Storage", 2016 IEEE International Symposium on Information Theory, 2644-2648.
Froeter et al., "Superior Neuronal Outgrowth Guidance and Rate Enhancement using Silicon Nitride Self-Rolled-up Membranes", 2015 IEEE, 93-94.
Gabrys and Milenkovic, "The Hybrid k-Deck Problem: Reconstructing Sequences from Short and Long Traces:", 2017 IEEE International Symposium on Information Theory (ISIT), IEEE, pp. 1-5.
Zhou et al., "Transient and Average Unsteady Dynamics of Single Polymers in Large-Amplitude Oscillatory Extension", Macromolecules, 2016, 49, 8018-8030.
Zhou and Schroeder, "Single polymer dynamics under large amplitude oscillatory extension", Physical Review Fluids 1, 2016, 053301-1-053301-17.
Yazdi et al., "A Rewritable, Random-Access DNA-Based Storage System", May 8, 2015, 26 pages.
Zhirnov et al., "Nucleic acid memory", Nature Materials, vol. 15, Apr. 2016, 366-370.
Orgel, Leslie E., "Molecular replication", Nature, vol. 358, Jul. 16, 1992, 203-209.
Mohseni et al., "III—As Pillar Arrays by Metal-Assisted Chemical Etching for Photonic Applications", Optical Society of America, 2013, 2 pages.
Zaharia et al., "Resilient Distributed Datasets: A Fault-Tolerant Abstraction for In-Memory Cluster Computing", Apr. 25-27, 2012, 14 pages.
Winfree et al., "Design and self-assembly of two-dimensional DNA crystals", Nature, vol. 394, Aug. 6, 1998, 539-544.
Yazdi et al., "Mutually Uncorrelated Primers for DNA-Based Data Storage", Sep. 13, 2017, 1-14.
Yaakobi et al., "On Codes that Correct Asymmetric Errors with Graded Magnitude Distribution", International Symposium on Information Theory Proceedings, 2011, IEEE, 1056-1060.
Tian et al., "Advancing high-throughput gene synthesis technology", Molecular BioSystems, 2009, 5, 714-722.
Van Hest and Tirrell, "Protein-based materials, toward a new level of structural control", Chem. Commun, 2001, 1897-1904.
Piccirilli et al., "Enzymatic incorporation of a new base pair into DNA and RNA extends the genetic alphabet", Nature, vol. 343, Jan. 4, 1990, 33-37.
Vaish et al., "Expanding the structural and functional diversity of RNA: analog uridine triphosphates as candidates for in vitro selection of nucleic acids", Nucleic Acids Research, 2000, vol. 28, No. 17, 3316-3322.
Balasundaram et al., "Porosity control in metal-assisted chemical etching of degenerately doped silicon nanowires", Nanotechnology, 23, 2012, 7 pages.
Huang et al., "Rolled-up transparent microtubes as two-dimensionally confined culture scaffolds of individual yeast cells", Lap Chip, 2009, 9, 263-268.

(56) References Cited

OTHER PUBLICATIONS

Soloveichik et al., "DNA as a universal substrate for chemical kinetics", PNAS Early Edition, approved Jan. 29, 2010 (received for review Aug. 18, 2009), 13 pages.
Shipman et al., "CRISPR-Cas encoding of a digital movie into the genomes of a population of living bacteria", Jul. 20, 2017, vol. 547, Nature, 14 pages.
Shenoy et al., "Stokes trap for multiplexed particle manipulation and assembly using fluidics", PNAS, Apr. 12, 2016, vol. 113, No. 15, 3976-3981.
Shenoy et al., "Characterizing the performance of the hydrodynamic trap using a control-based approach", Microfluid Nanofluid (2015) 18:1055-1066.
Sarathy et al., "Graphene Nanopores for Electronic Recognition of DNA Methylation", J. Phys. Chem B, 2017, 121, 3757-3763.
Qui et al., "Electrically Tunable Quenching of DNA Fluctuations in Biased Solid-State Nanopores", ACS Nano, 2016, 10 4482-4488.
Roy et al., "Design and synthesis of digitally encoded polymers that can be decoded and erased", Nature Communications, May 26, 2015, 8 pages.
Ross et al., "Characterizing and measuring bias in sequence data", Genome Biology, 2013, 20 pages.
Qiu et al., "Detection and mapping of DNA methylation with 2D material naopores", npj 2D Materials and Applications (2017)1:3, 8 pages.
Huang et al., "Nanomechanical Architecture of Strained Bilayer Thin Films: From Design principles to Experimental Fabrication", Adv. Mater., 2005, 17, 2860-2864.
Bulushev et al., "Single Molecule Localization and Discrimination of DNA-Protein Complexes by Controlled Translocation Through Nanocapillaries", Nano Lett., 2016, 7882-7890.
Reed and Solomon, "Polynomial Codes Over Certain Finite Fields", J Soc. Indust. Appl. Math., vol. 8, No. 2, Jun. 1960, 300-304.
Qian et al., "Neural network computation with DNA strand displacement cascades", Nature, vol. 475, Jul. 21, 2011, pp. 368-372.
Qian et al., "Computation with DNA Strand Displacement Cascades", Jun. 3, 2011, vol. 332, Science, pp. 1196-1201.
Phillips et al., "Scalable Molecular Dynamics with NAMD", J Comput Chem 26:1781-1802, 2005.
Perrin, "Lifelike but Not Living: Selection of Synthetically Modified Bioinspired Nucleic Acids for Binding and Catalysts", Polymer Science: A Comprehensive Reference, vol. 9, 2012, pp. 3-33.
Noren et al., "A General Method for Site-Specific Incorporation of Unnatural Amino Acids into Proteins", Science, vol. 244, Oct. 14, 2019, pp. 182-188.
Niu et al., "Enzyme-free translation of DNA into sequence-defined synthetic polymers structurally unrelated to nucleic acids", Nature Chemistry, vol. 5, Apr. 2013, pp. 282-292.
Hans Packer, "The gene construction revolution", Jul. 21, 2014, pp. 1-4.
Ohta et al., "Synthesis of biopolymers using genetic code reprogramming", Current Opinion in Chemical Biology, 2008, 12:159-167.
Hans Packer, "Decoding Cas9 orthologs using gBlocks Gene Fragments", Jan. 15, 2014, 1 page.
Organick et al., "Scaling up DNA data storage and random access retrieval", bioRxiv, Mar. 7, 2017, pp. 1-14.
Ma et al., "DNA synthesis, assembly and applications in synthetic biology", Current Opinion in Chemical Biology, 2012, 16:260-267.
Naydenova and Klove, "Generalized Bose-Lin Codes, a Class of codes Detecting Asymmetric Errors", IEEE Transactions on Information Theory, vol. 53, No. 3, Mar. 2007, pp. 1188-1193.
Marciel et al., "Template-Directed Synthesis of Structurally Defined Branched Polymers", Macromolecules, 2015, 48, 1296-1303.
Mikheyev and Yin, "A first look at the Oxford Naopore MinION sequencer", Molecular Ecology Resources (2014) 14, 1097-1102.
Milenkovic and Kashyap, "On the Design of Codes for DNA Computing", Ytrehus (Ed.): WCC 2005, LNCS 3969, pp. 100-119, 2006.
Mai et al., "Topology-Controlled Relaxation Dynamics of Single Branched Polymers", ACS Macro Lett., 2015, 4, 446-452.
Ma et al., "Error correction in gene synthesis technology", Trends in biotechnology, Mar. 2012, vol. 30, No. 3, 147-154.
Mao et al., "Models and information-theoretic bounds for nanopore sequencing", May 31, 2017, 58 pages.
Liu et al., "Geometrical Effect in 2D Nanopores", Nano Lett., 2017, 17 4223-4230.
Matsui et al., "Construction of saccharide-modified DNAs by DNA polymerase", Bioorganic & Medicinal Chemistry Letters 17, (2007) 456-460.
Mai and Schroeder, "Single polymer dynamics of topologically complex DNA", Current Opinion in Colloid & Interface Science 26 (2016) 28-40.
Barluenga et al., "PNA as a Biosupramolecular Tag for Programmable Assemblies and Reactions," Acc. Chem. Res., published May 7, 2015, pp. 1319-1311, vol. 48.
Holub et al., "Tricks with clicks: modification of peptidomimetic oligomers via copper-catalyzed azide-alkyne [3 + 2] cycloaddition," Soc. Rev., published online Mar. 4, 2010, pp. 1325-1337, vol. 39.
Peng et al. "A template-mediated click-click reaction : PNA-DNA, PNA-PNA (or peptide) ligation and single nucleotide discrimination," Eur. J. Org. Chem. 2010, pp. 4194-4197.

* cited by examiner

220

230

300

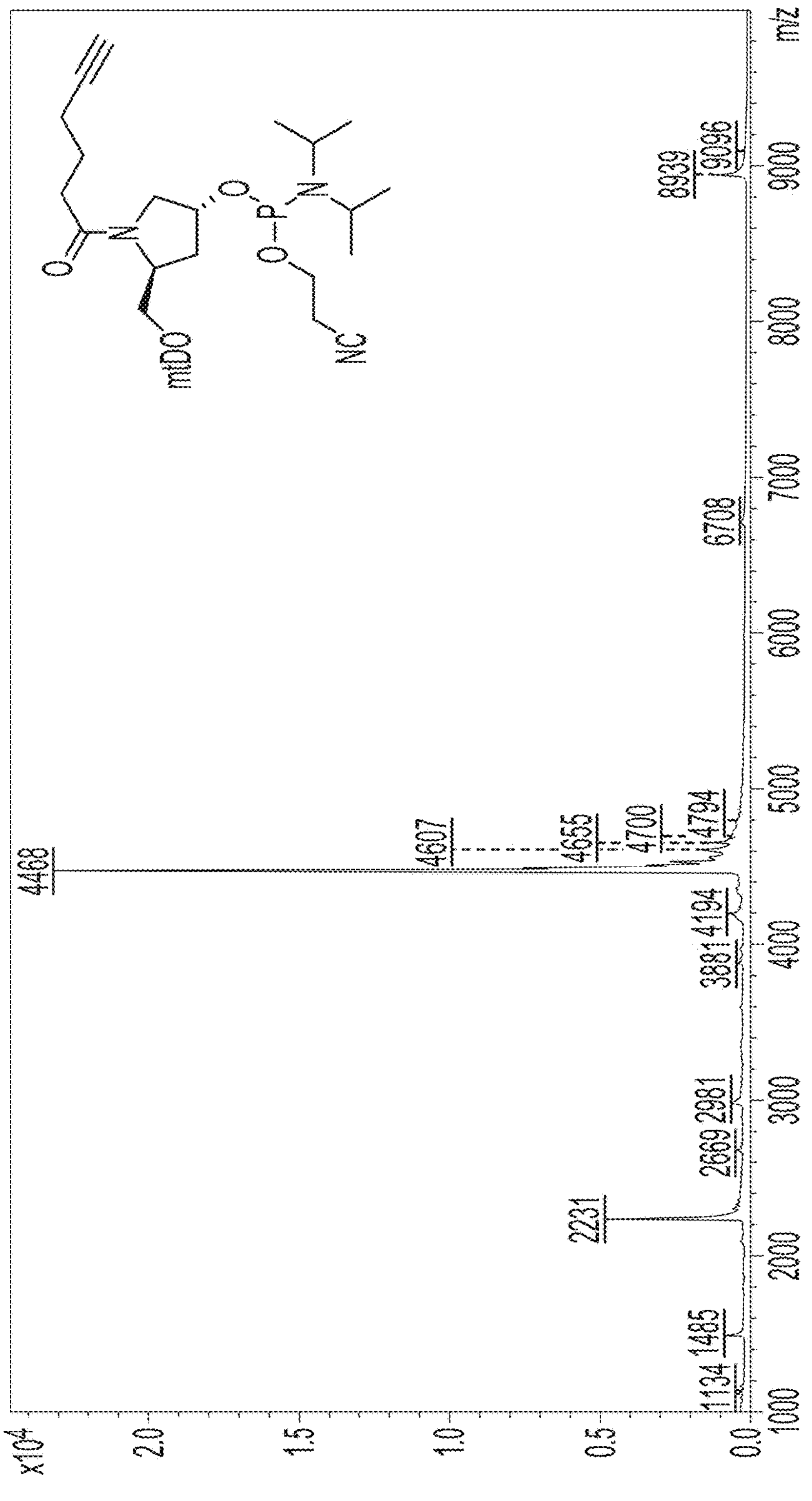

DNA sequence:AXC GCT ACT ACT ATT

X denotes an alkyne-modified abasic site

Molecular Mass M =4471

Chemically modified abasic oligonucleotides were synthesized via click chemistry of alkyne carrying phosphoramidites followed by solid-phase oligonucleotide synthesis Demonstrated viability of incorporating alkyne modification at different locations of an oligonucleotide

Figure 3A

DNA sequence: AAC GCT ACT ACX XXT
X denotes an alkyne-modified abasic site
Molecular Mass M =4409

520

522

530

SEQUENCE LISTING

```
Sequence total quantity: 3
SEQ ID NO: 1           moltype = DNA  length = 15
FEATURE                Location/Qualifiers
variation              1..15
                       note = Synthetic Oligonucleotide
variation              2
                       note = n can be any of A, C, G, or T and is an
                        alkyne-modified abasic site
source                 1..15
                       mol_type = other DNA
                       organism = synthetic construct
SEQUENCE: 1
ancgctacta ctatt                                             15

SEQ ID NO: 2           moltype = DNA  length = 15
FEATURE                Location/Qualifiers
variation              1..15
                       note = Synthetic Oligonucleotide
variation              12
                       note = n can be any of A, C, G, or T and is an
                        alkyne-modified abasic site
variation              13
                       note = n can be any of A, C, G, or T and is an
                        alkyne-modified abasic site
variation              14
                       note = n can be any of A, C, G, or T and is an
                        alkyne-modified abasic site
source                 1..15
                       mol_type = other DNA
                       organism = synthetic construct
SEQUENCE: 2
aacgctacta cnnnt                                             15

SEQ ID NO: 3           moltype = DNA  length = 20
FEATURE                Location/Qualifiers
misc_feature           1..20
                       note = Native Template
source                 1..20
                       mol_type = other DNA
                       organism = synthetic construct
SEQUENCE: 3
taccgggata tattagcgaa                                        20
```

ON-CHIP NANOSCALE STORAGE SYSTEM USING CHIMERIC DNA

CROSS-REFERENCE TO RELATED APPLICATIONS

This application is a continuation application of U.S. application Ser. No. 16/593,450, filed Oct. 4, 2019, the disclosure of which is explicitly incorporated by reference herein.

STATEMENT ON FEDERALLY SPONSORED RESEARCH OR DEVELOPMENT

This invention was made with Government support under Grant No. 1807526 (National Science Foundation). The Government has certain rights in the invention.

REFERENCE TO SEQUENCE LISTING

A computer readable form of the Sequence Listing is filed with this application by electronic submission and is incorporated into this application by reference in its entirety. The Sequence Listing is contained in the file created on Jul. 19, 2023, having the file name "19-1227-US-CON Sequence-Listing.xml" and is 6,391 bytes in size.

BACKGROUND

DNA molecules, which may be represented as paired strings over a four letter "base" alphabet {Adenine (A), Thymine (T), Guanine (G), Cytosine (C)}, stand out as candidates for massive macromolecular storage media due to a number of unique properties. DNA sequences have outstanding information integrity (genetic information was extracted from 30,000 year old Neanderthal bones and 700,000 years old horse bones) and they enable ultra-high information density (a cell nucleus with an average diameter of 5 μm hosts DNA strings encoding 6.4 GBs of information). There also exist well-developed accompanying DNA "writing" (DNA synthesis) and massive "reading" technologies (high throughput DNA sequencing).

However, little attention has been placed on addressing the biggest challenges encountered in all practical implementations of DNA-based data storage systems: the excessively large cost and delay of DNA synthesis (roughly $0.1/megabase, provided that the synthesized strands are of length ~2000 nucleotides (nts), with commercial synthesis times exceeding two days), and the incompatibility of DNA media with existing silicon computing architectures that support data access, retrieval, and computing.

SUMMARY

The present disclosure describes systems and methods that can provide portable, real-time DNA memories, among other possibilities.

In a first aspect, a deoxyribonucleic acid (DNA)-based data storage element is provided. The DNA-based data storage element includes a DNA backbone and a plurality of non-natural nucleic acids bioconjugated to the DNA backbone.

Optionally, at least one of the non-natural nucleic acids could include a peptide nucleic acid (PNA). In such scenarios, the PNA could include a peptide backbone and a plurality of natural nucleobase monomers.

Optionally, the DNA backbone could include single-stranded DNA.

Additionally or alternatively, the DNA backbone could include double-stranded DNA.

Optionally, the plurality of non-natural nucleic acids could include a structurally-defined branched polymer architecture.

In a second aspect, a microfluidic deoxyribonucleic acid (DNA)-based data storage system is provided. The DNA-based data storage system includes a loading region configured to receive a plurality of DNA-based data storage elements in a suspension fluid and a plurality of microtubes disposed in a capture/release region. The microtubes are configured to capture and release the DNA-based data storage elements. The DNA-based data storage system also includes a linearization region configured to linearize the DNA-based data storage elements and a readout region with a readout device configured to provide information indicative of the respective DNA-based data storage elements.

Optionally, at least one microtube of the plurality of microtubes comprises a self-rolled microtube. In such scenarios, in an initial condition, the self-rolled microtube could include a substrate, a sacrificial etch material overlaying the substrate, a compressive layer overlaying the sacrificial etch material, a tensile layer overlaying the compressive layer, and a plurality of electrodes. Furthermore, in a rolled condition, the self-rolled microtube could include at least a portion of the tensile and compressive layers rolled into a tubular shape having a diameter of less than 10 microns.

Optionally, the linearization region could include an array of linearization structures arranged between the capture/release region and the readout region.

Optionally, the readout device could include a solid-state nanopore device.

Optionally, the readout device could include a tandem mass spectrometry system.

In a third aspect, a method to synthesize a deoxyribonucleic acid (DNA)-based data storage element is provided. The method includes selecting an abasic site of a DNA backbone, modifying the abasic site to be compatible with bioconjugation by way of cycloaddition, and performing a bioconjugation so as to add at least one non-natural functional group to the abasic site as modified.

Optionally, the bioconjugation includes an azide-alkyne Huisgen-type cycloaddition.

Optionally, modifying the abasic site could be performed so as to form a bioconjugation click chemistry target. In such scenarios, performing the bioconjugation could include adding at least one peptide nucleic acid (PNA). The PNA includes a peptide backbone and a plurality of natural nucleobase monomers.

In a fourth aspect, a method is provided. The method includes dispensing a plurality of deoxyribonucleic acid (DNA)-based data storage elements in a suspension fluid into a loading region of a microfluidic DNA-based data storage system and causing at least one microtube of a plurality of microtubes disposed in a capture/release region of the DNA-based data storage system to capture at least one DNA-based data storage element. The method also includes causing the at least one microtube to release the at least one DNA-based data storage element and receiving, from a readout device disposed proximate to a readout region of the DNA-based data storage system, information indicative of data stored with the at least one DNA-based data storage element.

Optionally, causing the at least one microtube to capture or release the at least one DNA-based data storage element could include biasing a plurality of electrodes of the at least one microtube so as to capture or release the at least one DNA-based data storage element, respectively.

Optionally, method further includes causing the at least one microtube to hold the at least one DNA-based data storage element within the at least one microtube.

Other aspects, embodiments, and implementations will become apparent to those of ordinary skill in the art by reading the following detailed description, with reference where appropriate to the accompanying drawings.

BRIEF DESCRIPTION OF THE FIGURES

FIG. 3A illustrates chemically-modified abasic oligonucleotides (SEQ ID NO.: 1) synthesized via click chemistry of alkyne carrying phosphoramidites followed by solid-phase oligonucleotide synthesis, according to an example embodiment.

DETAILED DESCRIPTION

Figure 1:
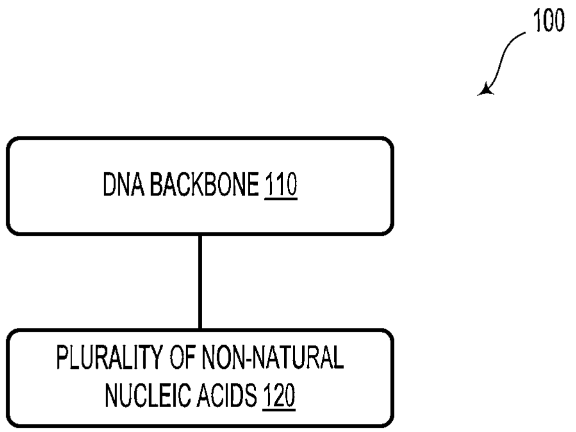
FIG. 1 illustrates a DNA-based data storage element, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. Overview

We are in the midst of a data revolution that has produced unprecedented amounts of new information: some estimate that as much as 90% of the world's data has been created in the last few years. Facebook alone generates 4 PB of data every day. Data generated from DNA sequencing projects is doubling every seven months, and is expected to reach the 2 exabytes per year threshold in the next decade. Furthermore, by 2021, the global internet protocol (IP) traffic will exceed 278 EB per month or 3.3 ZB per year, which is more than two orders of magnitude higher than what it was in 1992. This rapid proliferation of data has had enormous impacts on the development of data storage technologies, and is currently pushing the boundaries of our search for new ultra-dense storage media. One promising direction in this quest is macromolecular data storage, the key principles of which have been outlined by the physicist Richard Feynman. DNA molecules, which may be abstracted as paired strings over a four letter "base" alphabet {A, T, G, C}, stand out as candidates for massive macromolecular storage media due to a number of unique properties. DNA sequences have outstanding information integrity (genetic information was extracted from 30,000 years Neanderthal and 700,000 years old horse bones), they enable ultra-high density (a cell nucleus with an average diameter of 5 μm hosts DNA strings encoding 6.4 GBs of information). There also exist well-developed accompanying DNA "writing" (DNA synthesis) and massive "reading" technologies (high throughput DNA sequencing). Furthermore, as of now, DNA and its derivatives are the only known macromolecules that enable random access to select parts of the information content and large-scale amplification via polymerase chain reactions (PCRs). DNA has also been shown to lend itself to portable storage architectures with controllable data access, rewriting, and management, all in the presence of a large number of insertion/deletion errors inherent to inexpensive nanopore sequencers. Furthermore, DNA molecules have been used as a building blocks for a number of self-assembly architectures and DNA-strand displacement computational networks.

The present disclosure provides systems and methods that can help make DNA memories portable and operational in real time. For example, the present disclosure provides a new model for DNA-based memory storage termed "chimeric DNA storage". Chimeric DNA storage utilized an expanded alphabet of bases by utilizing single-stranded native DNA strands (e.g., M13 bacteriophage genomic DNA consisting of about 7200 bases). Namely, in some embodiments, DNA bases could be modified in different ways to increase component diversity. For example, chemical modifications may be made along the DNA backbone to increase data storage capacity. In such scenarios, a variable number of alkyne modifications may be incorporated at different locations within an oligonucleotide.

Several architectures for biological or solid state nanopores are described that can enable detection of chemical changes in chimeric DNA and structural changes, such as DNA nicks. Some embodiments may include random access, controlled transportation, sample preparation and chimeric DNA sequencing, utilizing bio-compatible self-rolled-up membranes (S-RuMs) and specialized nanopore sequencers. As an example, planar, multilayered, patterned surface structures containing several layers of silicon nitride ($SiN_x$) that allow for the formation of grids of micro and nanotubes. Flexible grids of micro/nanotube structures could be controlled by way of 3D nanoelectrodes that could enable DNA string access and transfer and precisely controlled sample preparation.

II. Example DNA-based Data Storage Elements

FIG. 1 illustrates a DNA-based data storage element 100, according to an example embodiment. As described herein, the DNA-based data storage element 100 could provide a new storage paradigm termed "chimeric DNA storage." The DNA-based data storage element 100 could include a DNA backbone 110. For example, the DNA backbone 110 of the DNA-based data storage element 100 could include a single-stranded native DNA strand (e.g., M13 bacteriophage genomic DNA consisting of 7200 bases), termed the template. Such template DNA is readily and inexpensively available as it does not need to be synthesized. However, other DNA backbones are possible and contemplated.

The DNA-based data storage element 100 could also include a plurality of non-natural nucleic acids 120 bioconjugated to the DNA backbone 110. That is, coupled to each template, a large number of complementary oligos (e.g., short single stranded DNA (ssDNA) of length≤20) are hybridized, with each oligo containing different combinations of chemically modified nucleotides.

In some embodiments, chemically modified short DNA oligos can be easily generated at large scale and using automated solid-phase synthesis, followed by automated robotic handling for utilizing chemically modified oligos for different coding sequences.

As an illustrative example, assume that the native template is 3'-AAGCGATTATATAGGGCCAT-5' (SEQ ID NO.: 3) and that each nucleotide comes in two different chemically modified forms, say $A_1$, $A_2$, $T_1$, $T_2$, $C_1$, $C_2$ and $G_1$, $G_2$. If the oligos are of length four, then the first oligo to hybridize to the template 3' end has to be TTCG, with the user data specifying which combination from $T_1T_1C_1G_1$, $T_1T_1C_1G_2$, $T_1T_1C_2G_1$, . . . to use.

With this approach, one can very effectively increase the alphabet size: if each oligo contains all four types of bases, and n chemical modifications for each nucleotide are available, the alphabet increases from 4 to $n^4$, and each oligo is a symbol of the alphabet.

In some embodiments, at least one of the non-natural nucleic acids 120 may include a peptide nucleic acid (PNA). In such scenarios, the PNA may include a peptide backbone and a plurality of natural nucleobase monomers.

As described above, the DNA backbone 110 could include single-stranded DNA. However, in other embodiments, the DNA backbone 110 could additionally or alternatively include double-stranded DNA.

In various examples, the plurality of non-natural nucleic acids 120 could include a structurally-defined branched polymer architecture.

Furthermore, in some embodiments, chemically modified single-stranded DNA oligos can be obtained as follows. In general, chemically modified abasic oligonucleotides can be synthesized via "click" chemistry of alkyne-functionalized phosphoramidites followed by solid-phase oligonucleotide synthesis.

First, functional groups that are responsible for data encoding are covalently linked onto the terminal alkynes of abasic phosphoramidites via copper-catalyzed azide-alkyne Huisgen cycloaddition, yielding phosphoramidites with a diverse set of possible chemical modifications. Such a cycloaddition could include, for example, a 1,3-dipolar cycloaddition between an azide and a terminal or internal alkyne to provide a 1,2,3-triazole.

Second, a long strand of sequence-defined chemically modified oligonucleotides could be synthesized using automated solid-phase synthesis. As described herein, solid-phase synthesis could include one or more methods in which molecules are covalently bound on a solid support material and synthesized by utilizing a sequential, step-wise approach in a single reaction vessel.

In example embodiments, the exact sequence of chemical modifications in the non-natural nucleic acids 120 (e.g., oligonucleotide strands) precisely encodes the information stored in the macromolecule. Using this approach, chemical synthesis of non-natural abasic oligonucleotides allows for the ability to incorporate a wide range of chemical modifications. In such scenarios, the amount of information content (and corresponding storage capacity in sequence-defined macromolecules) can be greatly increased.

The viability of incorporating a variable number of alkyne modifications at different locations within an oligonucleotide has been studied in relation to this work. In such studies, the coupling efficiency of alkyne-modified phosphoramidites was high enough to allow for the synthesis of oligonucleotides containing multiple adjacent chemical modifications along the same DNA backbone 110. This property beneficially provides enhanced flexibility in DNA sequence design and synthesis for increasing data storage capacity. Moreover, it has been reported that the alkyne-modified oligonucleotide is stable in aqueous solution for more than 1 year at −20° C., making this general approach and chemical platform suitable for long-term data storage.

Nature has produced only four natural nucleobases for DNA and twenty natural amino acids for proteins. Nevertheless, researchers have developed a series of methods to synthesize sequence-defined polymers with significantly larger chemical diversity based on biological methods. In one such method, a DNA backbone was used as a template for hybridization of non-natural nucleic acids or peptide nucleic acids (PNAs) which contain a peptide backbone and natural nucleobase monomers. This approach has been extended to allow synthesizing long chains of sequence-defined polymers using DNA templates in the absence of enzymes (i.e., PCR-free processes). In an alternative direction, enzymes such as DNA polymerase were utilized for incorporation of non-natural nucleotides, albeit with a limited range of chemical functionality due to challenges in natural polymerases recognizing "exotic" non-natural monomers.

PCR has been successfully used to incorporate a range of chemically modified nucleotides with sugars, fluoroalkanes, thiols, and aromatic groups. However, most of these demonstrations have included the incorporation of a single modified nucleotide at a single position. In some cases, researchers observed the so-called "nearest-neighbor effect," wherein the presence of a modified base at position (i−1) affects or inhibits the incorporation of a second modified base at position i. For these reasons, it can be challenging to incorporate arbitrary or widely differing chemistries of non-natural nucleotides using PCR. In the realm of non-natural amino acid incorporation into proteins, tremendous progress has been made in introducing multiple synthetic amino acid residues via repurposed amber codons.

In parallel, progress in the field of synthetic polymer chemistry has enabled methods for synthesizing biological or non-biological sequence-defined polymers with fairly high yields. A major benefit of synthetic sequence-defined polymers is their ability to access materials with broad chemical diversity, and expand far beyond the four natural nucleobases of DNA. To this end, solid-phase synthesis allows for the generation of precisely defined polymers with controlled primary monomer sequences. Utilizing this approach, iterative synthesis is used to covalently link select monomers to a solid (insoluble) support in successive chemical reactions, thereby yielding a long macromolecule chain with a precisely defined sequence. Iterative synthesis is common in nucleic acid (DNA, RNA) oligomer synthesis via standard protection/deprotection chemistry based on phosphoramidites. Furthermore, solid-phase synthesis can be easily extended to incorporate non-natural monomers, including the direct incorporation of chemically modified nucleobases in the interior of non-natural nucleotides or entirely synthetic polymers. Recently, an automated oligomer/molecule synthesizer termed "Molecule Maker", capable of producing a wide array of chemically distinct compounds including antibiotics and pi-conjugated polymers has been developed. Taken together, chemical synthesis methods based on solid-phase automated iterative chemistry provide an ideal platform to generate a wide array of non-natural sequence-defined polymers for information storage.

Figure 2A:
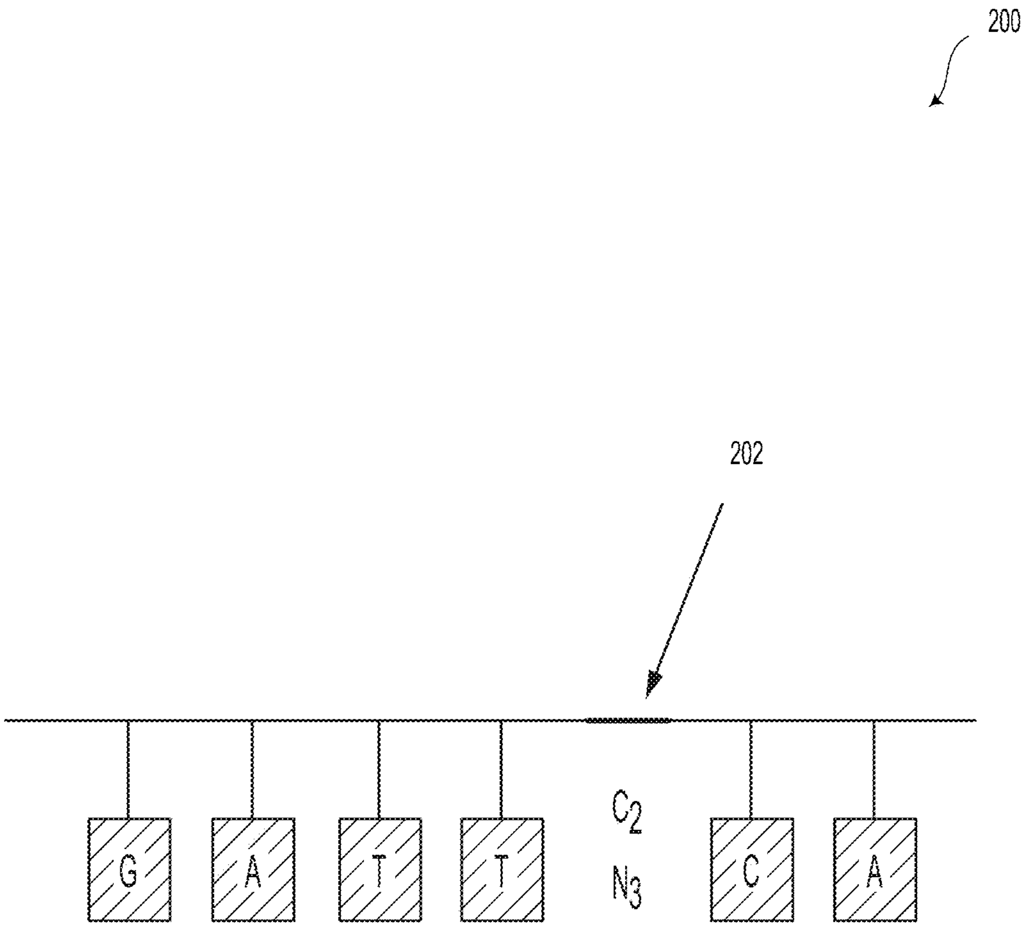
FIG. 2A illustrates a DNA strand with an azide-alkyne-modified abasic site, according to an example embodiment.

FIGS. 2A-2D illustrate various chemical modifications that can be made to DNA oligomers to encode information within the scope of the present disclosure. For example, FIG. 2A illustrates a DNA strand 200 with an azide-alkyne-modified abasic site 202.

Figure 2B:
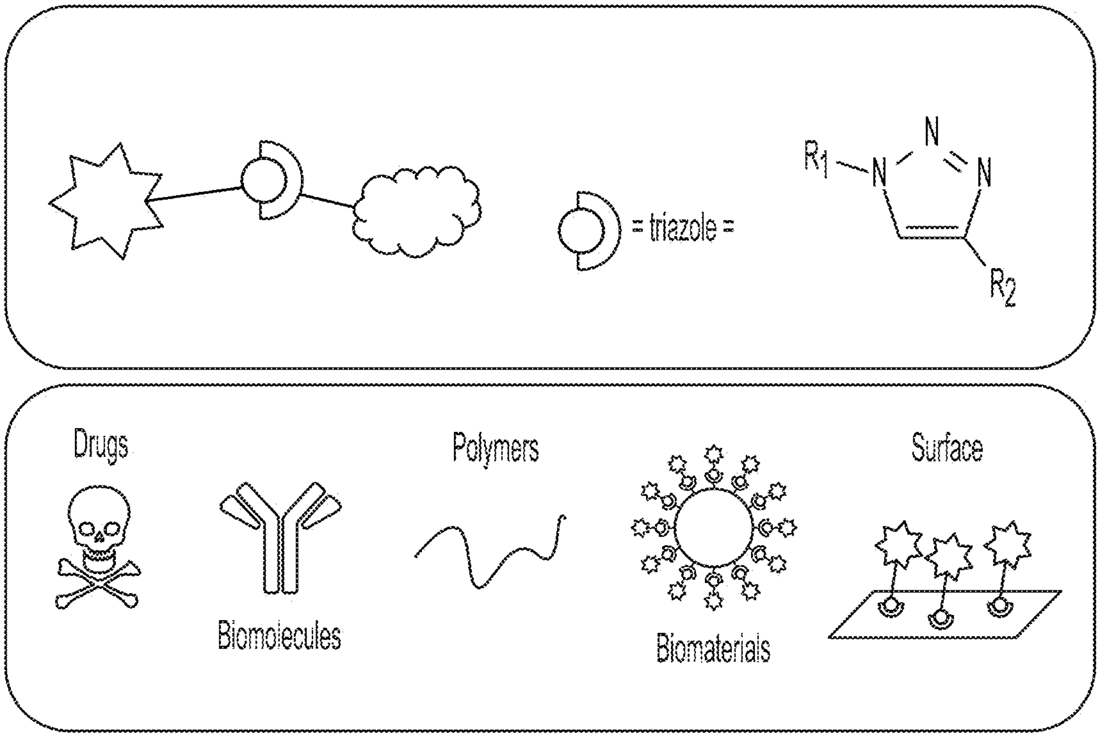
FIG. 2B illustrates an azide-alkyne-modified abasic monomer and click-chemistry sites, according to an example embodiment.

FIG. 2B illustrates azide-alkyne-modified abasic monomer and click-chemistry sites 220, according to an example embodiment.

Figure 2C:
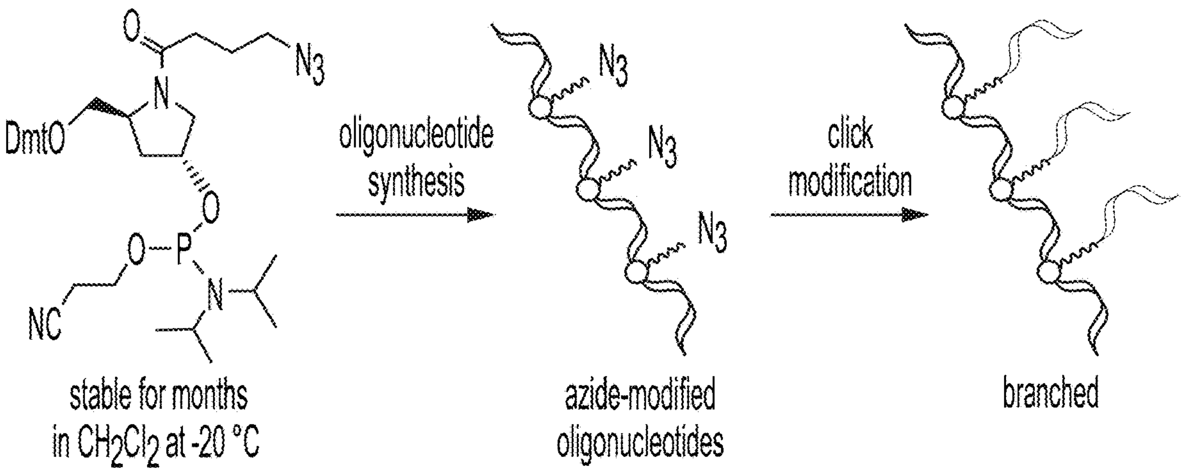
FIG. 2C illustrates click chemistry modifications, according to an example embodiment.

FIG. 2C illustrates click chemistry modifications 230, according to an example embodiment.

Figure 2D:
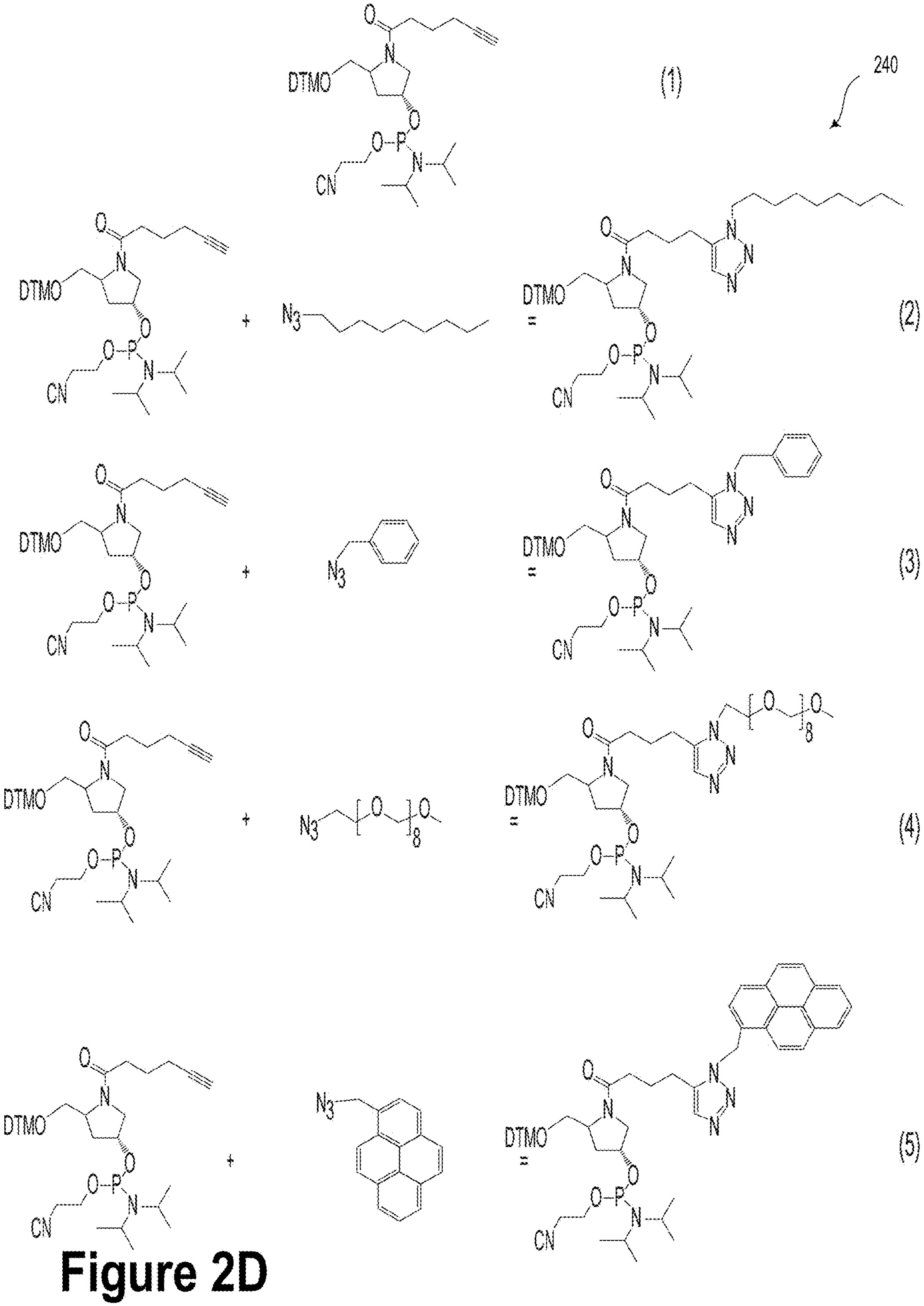
FIG. 2D illustrates potential chemistry modifications, according to an example embodiment.

FIG. 2D illustrates potential chemistry modifications 240, according to an example embodiment. The potential chemistry modifications 240 include examples of chemically-modified abasic monomers. It will be understood that although embodiments described herein may relate to alkyne/azide chemistry, other types of "click" chemistries are possible and contemplated within the scope of the present disclosure. For example, other potential chemistries could include, without limitation, alkene/azide chemistries, alkene (e.g., norbornene)/tetrazine chemistry, alkene/thiol chemistry, alkyne/thiol chemistry, etc.

FIG. 3A illustrates chemically-modified abasic oligonucleotides 300 synthesized via click chemistry of alkyne-carrying phosphoramidites followed by solid-phase oligonucleotide synthesis, according to an example embodiment.

Figure 3B:
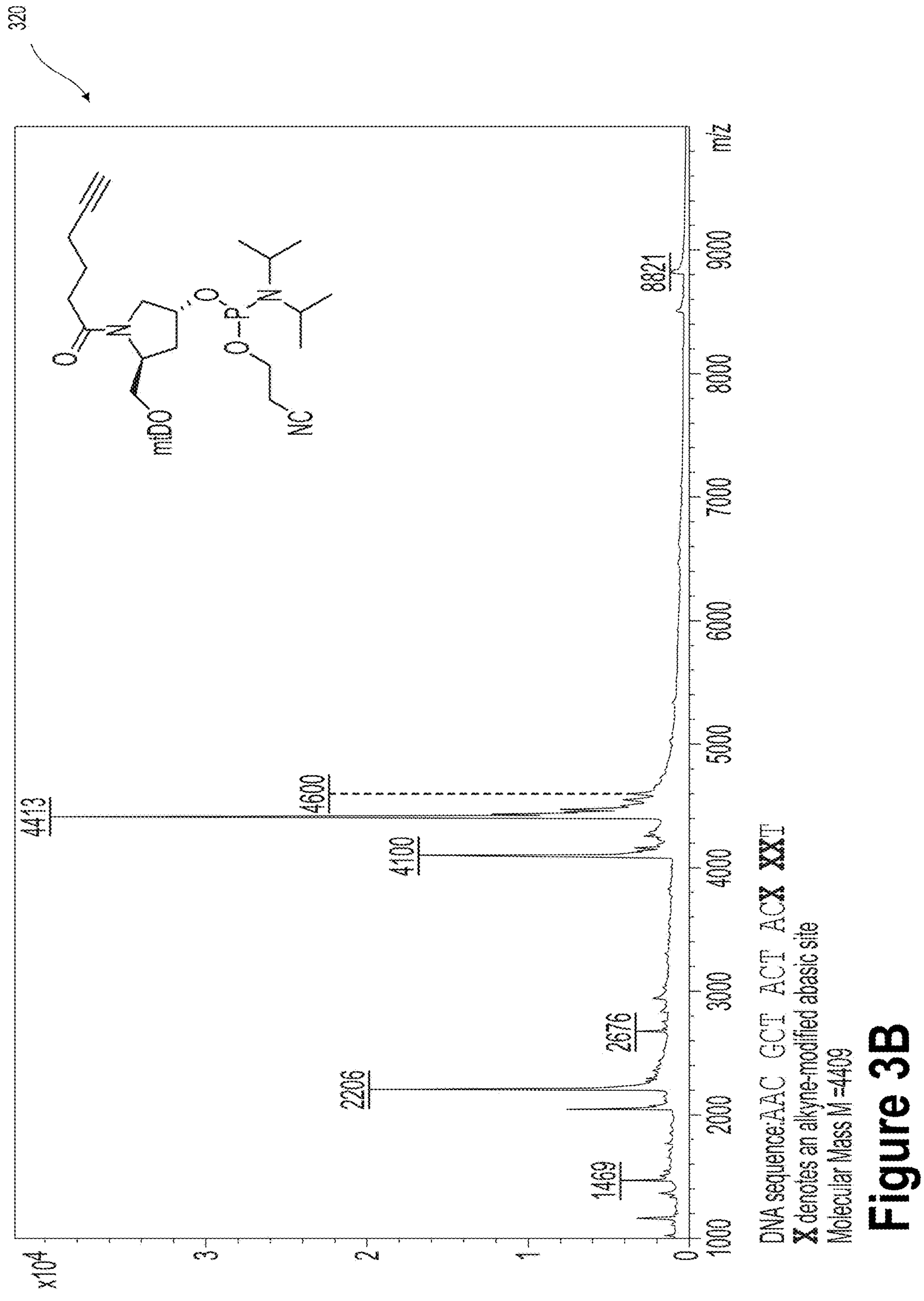
FIG. 3B illustrates chemically-modified abasic oligonucleotides (SEQ ID NO.: 2) synthesized via click chemistry of alkyne carrying phosphoramidites followed by solid-phase oligonucleotide synthesis, according to an example embodiment.

FIG. 3B illustrates chemically-modified abasic oligonucleotides 320 synthesized via click chemistry of alkyne-carrying phosphoramidites followed by solid-phase oligonucleotide synthesis, according to an example embodiment.

As described herein, the DNA-based data storage element 100 could be configured to leverage one or more symbol- and/or codeword-level error-correction schemes. For example, to understand how coding may improve the robustness of chimeric DNA storage, consider the example involving the template sequence 3'-(AAGC) (GATT) (ATAT) (AGGG) (CCAT)-5' (SEQ ID NO.: 3). In each 4-block of nucleotides, a different combination of nucleotide modifications $A_i$, $T_j$, $G_k$, and $C_l$, with integers i, j, k, l, is used. The type of modification within each block is fixed (e.g., $(A_1A_1G_2C_3)$ or $(A_7G_2G_2G_2)$). Each block may be viewed as a symbol from a large alphabet, and the representation of the symbol may contain built in redundancy at the individual base-encoding level: for example, in $(A_7G_2G_2G_2)$, one only needs to estimate the type of one G base correctly in order to deduce the type of all remaining G bases. The exact nucleotide sequence is fixed by the template so that some blocks may contain different numbers of A, T, G, and C's, which can provide nonuniform length repetition patterns. Furthermore, given that many different chemical modifications are possible, one can restrict the combinations of modifications to a constrained set that will further improve the probability of correct recovery (e.g., one may require each block to contain a shift of modifications of the form $A_i$, $T_{i+1}$, $G_{i+2}$, and $C_{i+3}$; in this case, it suffices to recover the chemical modification in one of the bases, and this can be the base with the largest frequency of repetition).

New asymmetric Reed-Solomon or other types of error correction codes may be used at the string (codeword) level. Furthermore, multiple traces (reads) of the same sequence obtained from the nanopore(s) may be combined into a consensus sequence and jointly corrected for errors, following iterative alignment and error-correction protocols.

III. Example DNA-based Data Storage Systems

Figure 4:
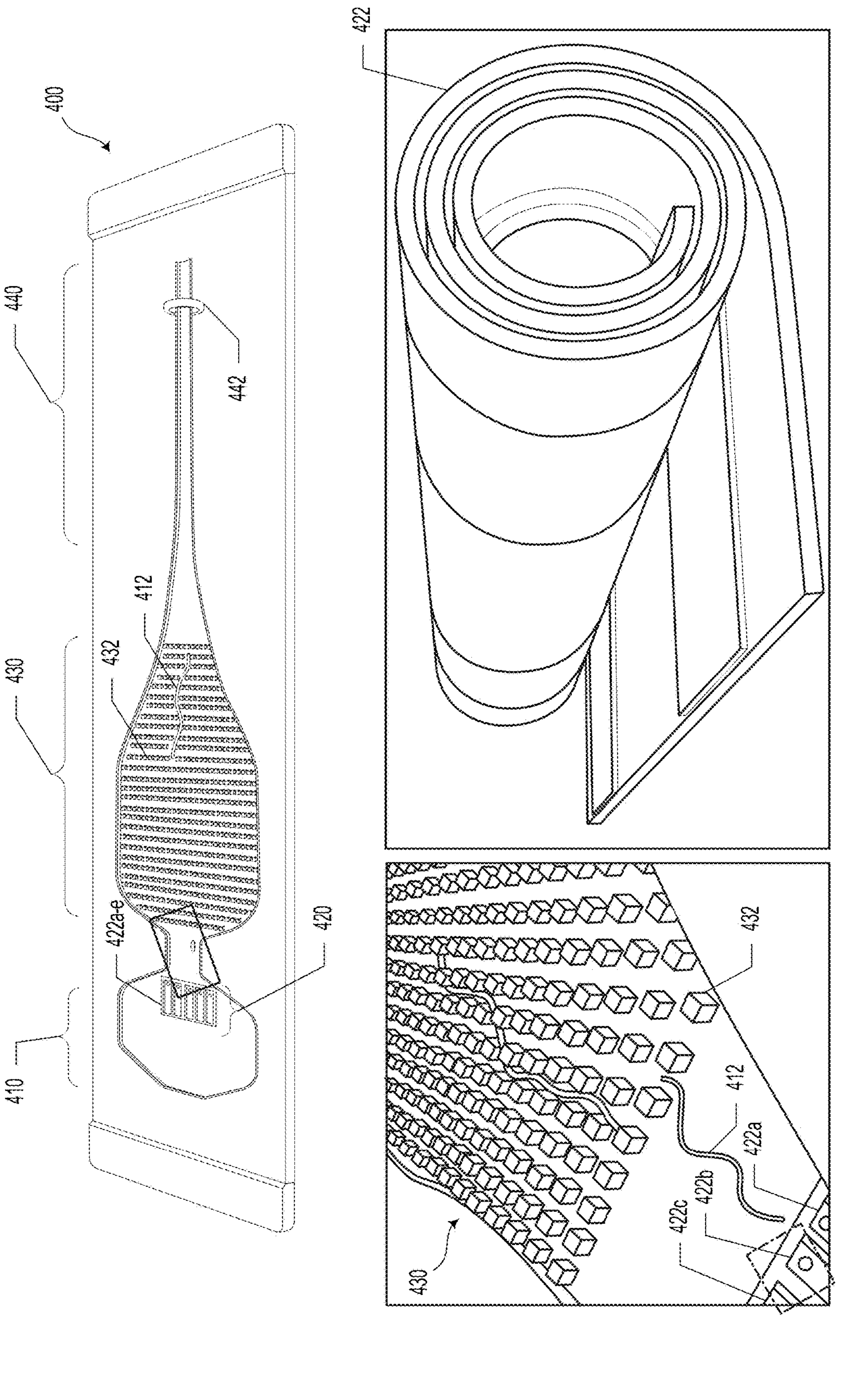
FIG. 4 illustrates a DNA-based data storage system, according to an example embodiment.

FIG. 4 illustrates a DNA-based data storage system 400, according to an example embodiment. In some embodiments, the DNA-based data storage system 400 could incorporate grids of nanomembrane tubes, on-chip sample preparation, and nanopore sequencing capabilites. For example, the DNA-based data storage system 400 includes a loading region 410 configured to receive a plurality of DNA-based data storage elements (e.g., DNA-based data storage element 100) in a suspension fluid. In some embodiments, the DNA-based data storage system 400 could represent a chimeric DNA-based data storage architecture.

The DNA-based data storage system 400 also includes a plurality of microtubes 422*a-e* disposed in a capture/release region 420. In example embodiments, DNA content could be guided into the microtubes by way of fluid flow and/or electrical fields. In such scenarios, the microtubes 422*a-e* could be configured to capture and release the DNA-based data storage elements. While FIG. 4 illustrates five microtubes 422*a-e*, it will be understood that more or fewer microtubes 422 are possible and contemplated.

In some embodiments, the microtubes 422 could be bio-compatible self-rolled-up membranes (S-RuMs) as described herein. However, it will be understood that other types of micro or nanotubes are possible and contemplated. In some embodiments, the microtubes 422 could include several components such as planar, multilayered, patterned surface structures containing several layers of silicon nitride ($SiN_x$) that allow for the formation of grids of micro and nanotubes.

In such scenarios, the DNA-based data storage system 400 may be configured to distribute chimeric DNA into different microtubes 422 according to its content, perform DNA concentration queries, and transport DNA to nanopore sequencing units. In various embodiments, each of these functionalities can be performed in real time and at scale. For each microtube 422, sequence loading, selection, and release can be accomplished by utilizing individually addressable embedded 3D cuff electrodes that guide DNA into tubes or release DNA in the microfluidic channel sequencing channel as illustrated in FIG. 4.

The DNA-based data storage system 400 additionally includes a linearization region 430 configured to linearize the DNA-based data storage elements. In some embodiments, the linearization region 430 could be similar or identical to Quantum Biosystems (QB) architecture, which is configured to denature and linearize the DNA. For example, in some embodiments, the linearization region 430 includes an array of linearization structures 432 arranged between the capture/release region 420 and a readout region 440.

The DNA-based data storage system 400 further includes that the readout region 440 has at least one readout device 442. In some embodiments, the readout device 442 could include a nanopore configured to provide information indicative of the respective DNA-based data storage elements. In example embodiments, the linearized ssDNA (e.g., DNA-based data storage elements 100) may be guided to a specially designed nanopore that is optimized for detection of structural changes in DNA nucleotides.

In example embodiments, the readout device 442 could include a solid-state nanopore device. In some embodiments, the solid-state nanopore device could include a nanopore sequencer. Additionally or alternatively, the readout device 442 could include a tandem mass spectrometry system.

In various examples, the location, dimensions, and/or method of operation of the readout device 442 could be configured to detect such structural changes in DNA nucleotides and not necessarily configured to reliably determine the bases along the DNA nucleotide (e.g., base calling). As described herein, the readout device 442 could be operated based on prior information (e.g., knowledge of the template DNA sequence) and with large redundancy because the chemical modifications in each nucleotide within one synthetic oligo are the same.

In some embodiments, the DNA-based data storage system 400 may be adapted to operate on RNA, proteins, or cellular complexes, as all these macromolecules are charged. For example, in some embodiments, the readout device 442 could include solid state and/or protein nanopores, which may be designed for sensing many other macromolecular structures. The utilization of other charged macromolecules are possible and contemplated within the context of the present disclosure.

Figure 5A:
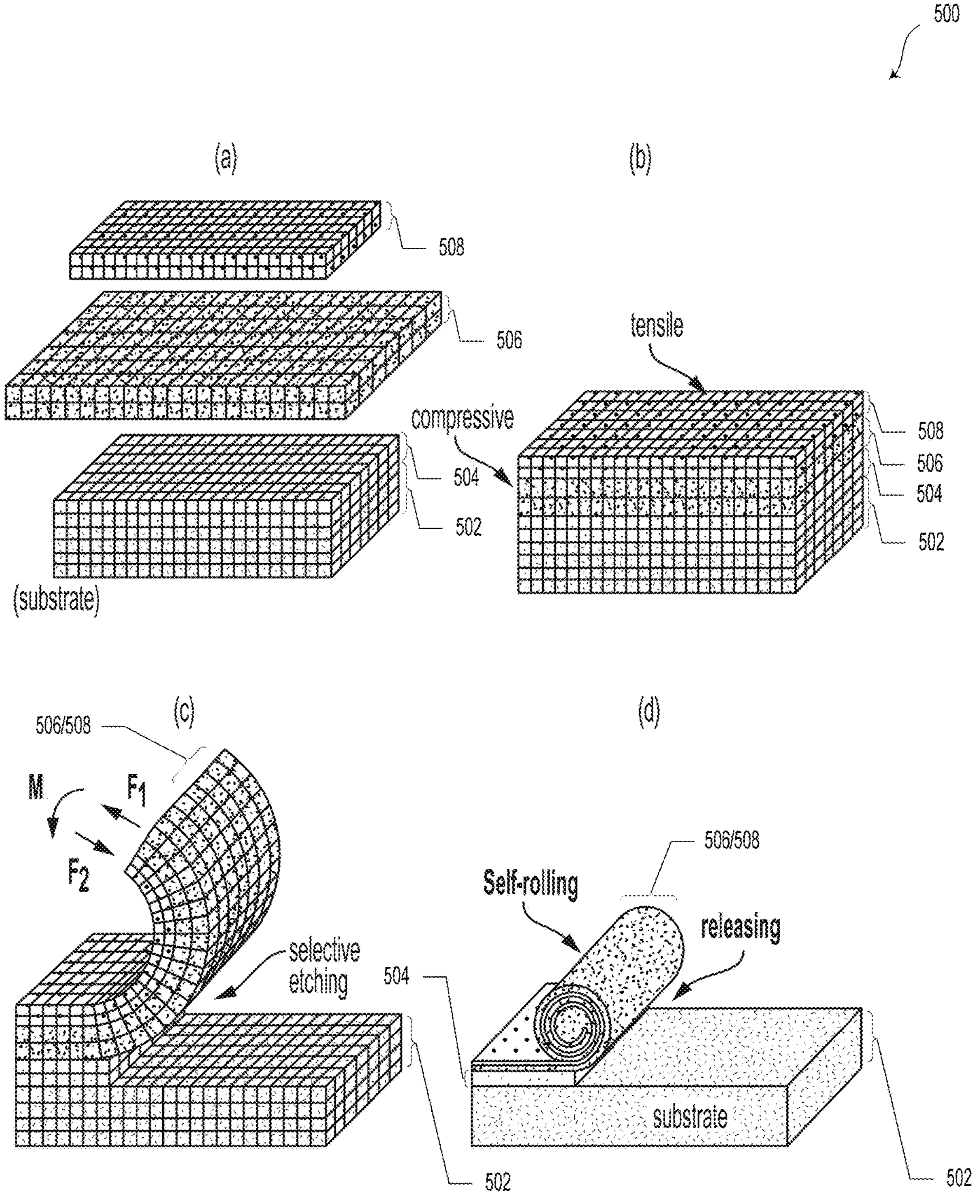
FIG. 5A is a schematic illustration of the strain-driven self-rolling-up mechanism, according to an example embodiment.

FIG. 5A is a schematic illustration of a self-rolled microtube 500. In some embodiments, at least one microtube 422 of the plurality of microtubes 422*a-e* could include a self-rolled microtube 500. In various examples, the self-rolled microtube could be formed by way of a strain-driven self-rolling-up mechanism, as described herein.

As described herein, the self-rolled microtube 500 or bio-compatible self-rolled-up membranes (S-RuM) could include micro/nanostructures that form based, at least in part, on a strain-driven mechanism where a bilayer of oppositely strained thin film membrane self-assembles into a cylindrical shape upon releasing from the substrate as illustrated in FIG. 5A, parts (c) and (d).

Figure 5B:
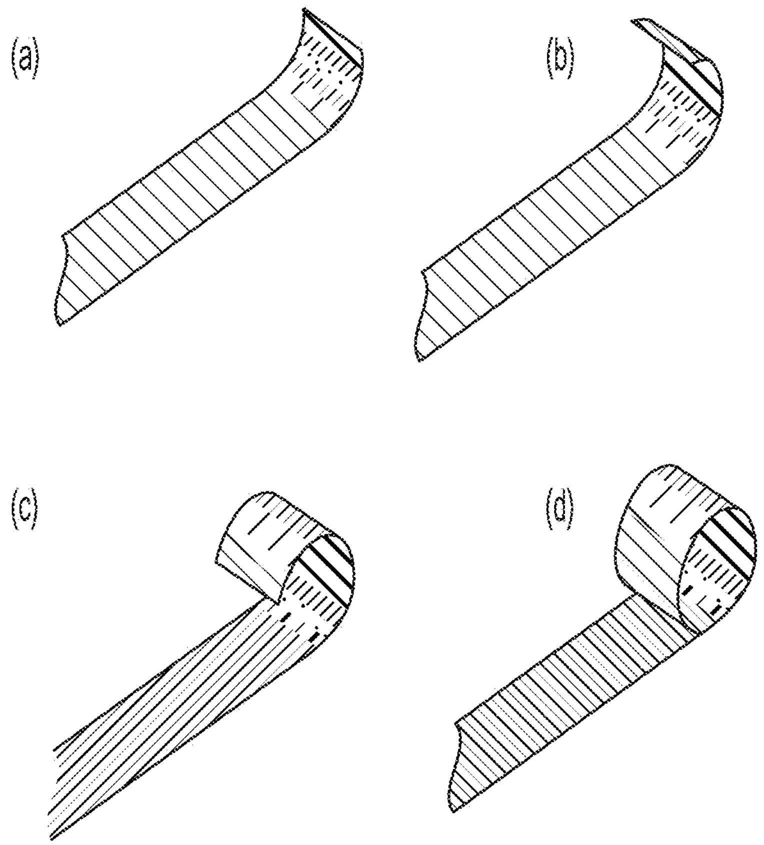
FIG. 5B illustrates FEM modeled S-RuM tube formation and a scanning electron microscopy (SEM) image of fabricated $SiN_x$ S-RuM tubes, according to an example embodiment.
Figure 5B:
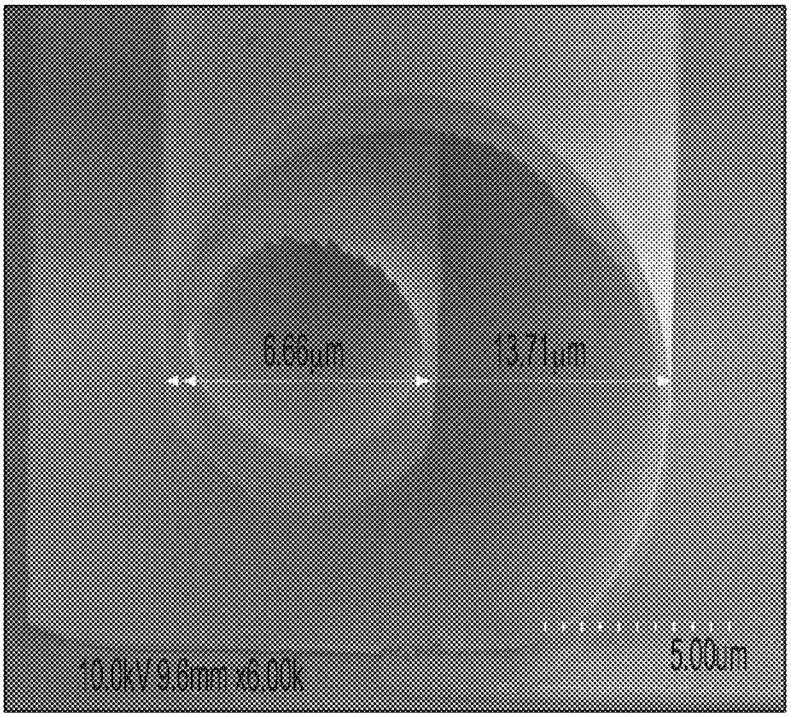

The curvature of an S-RuM is determined by the thickness of the layer and inversely proportional to the net strain in the membrane. The wall thickness of a rolled-up dielectric tube is between 1-100 nm, which yields a tube diameter of roughly 0.5-10 μm, although tubes of diameter as small as 3 nm have been fabricated. The number of rotations/turns in the tubes can be controlled by predefining the size and shape of the membranes before rolling up, as well as through etching control of a sacrificial layer 504. A transient finite element method (FEM) solver was developed to accurately predict the dimension of the S-RuM tubes and to guide the fabrication process 520 as illustrated in FIG. 5B.

The benefits of this platform include the 3D structural versatility, hierarchical integration of functional materials and layouts, all using a fabrication process flow that is compatible with industrial planar process technology. Such systems also enable miniaturization of passive electronic components and photonic integration.

In such scenarios, in an initial condition (illustrated in FIG. 5A, parts (a) and (b)), the self-rolled microtube 500 includes a substrate 502, a sacrificial etch material 504 overlaying the substrate 502, a compressive layer 506 overlaying the sacrificial etch material 504, a tensile layer 508 overlaying the compressive layer 506, and a plurality of electrodes 562.

Additionally, in a rolled condition (illustrated in FIG. 5A, parts (c) and (d)), the self-rolled microtube 500 includes at least a portion of the tensile layer 508 and the compressive layer 506 being rolled into a tubular shape having a diameter of less than 10 microns.

FIG. 5B illustrates finite element model (FEM) modeled S-RuM tube formation 520 and a scanning electron microscopy (SEM) image 522 of fabricated $SiN_x$ S-RuM tubes, according to an example embodiment.

Figure 5C:
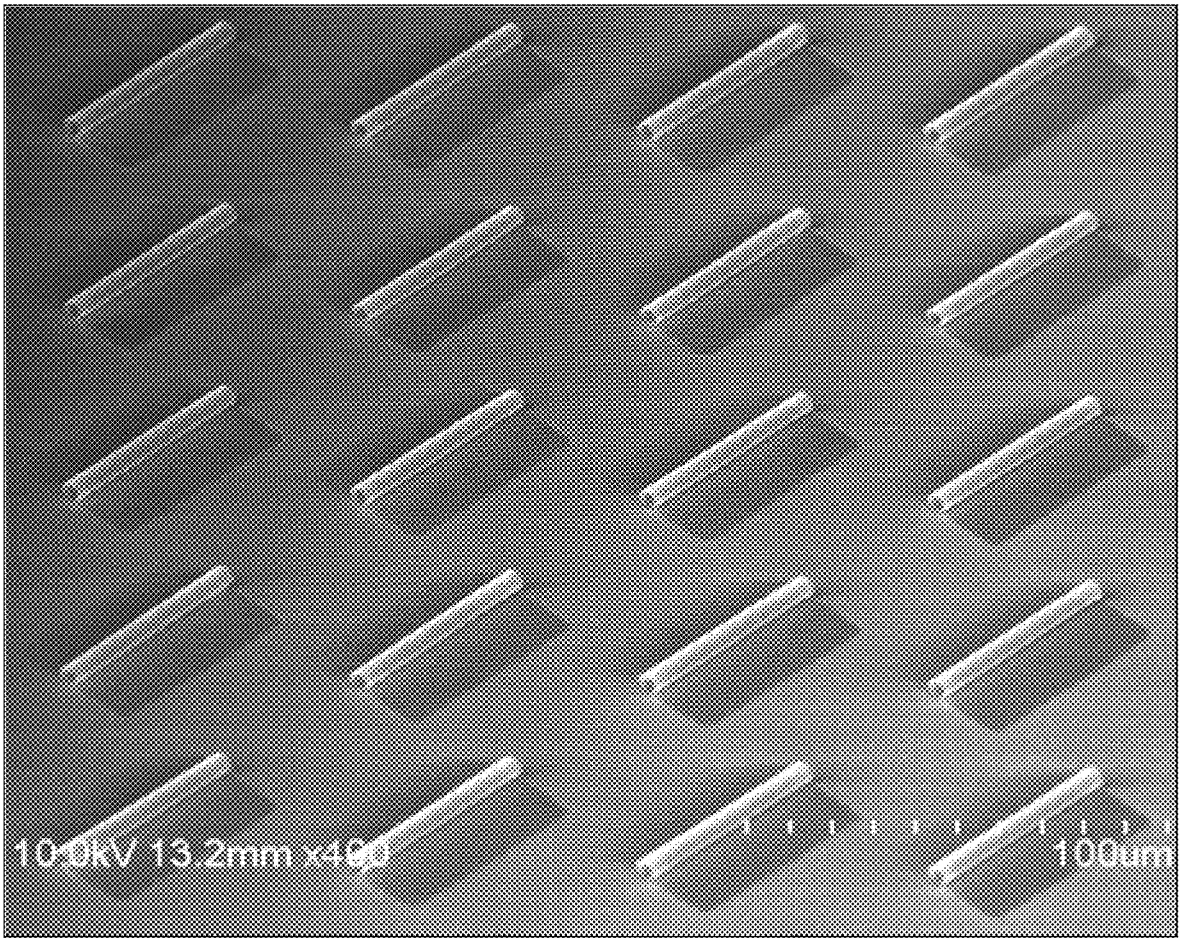
FIG. 5C is an SEM image of fabricated $SiN_x$ S-RuM tubes, according to an example embodiment.

FIG. 5C is an SEM image 530 of fabricated $SiN_x$ S-RuM tubes, according to an example embodiment.

Figure 5D:
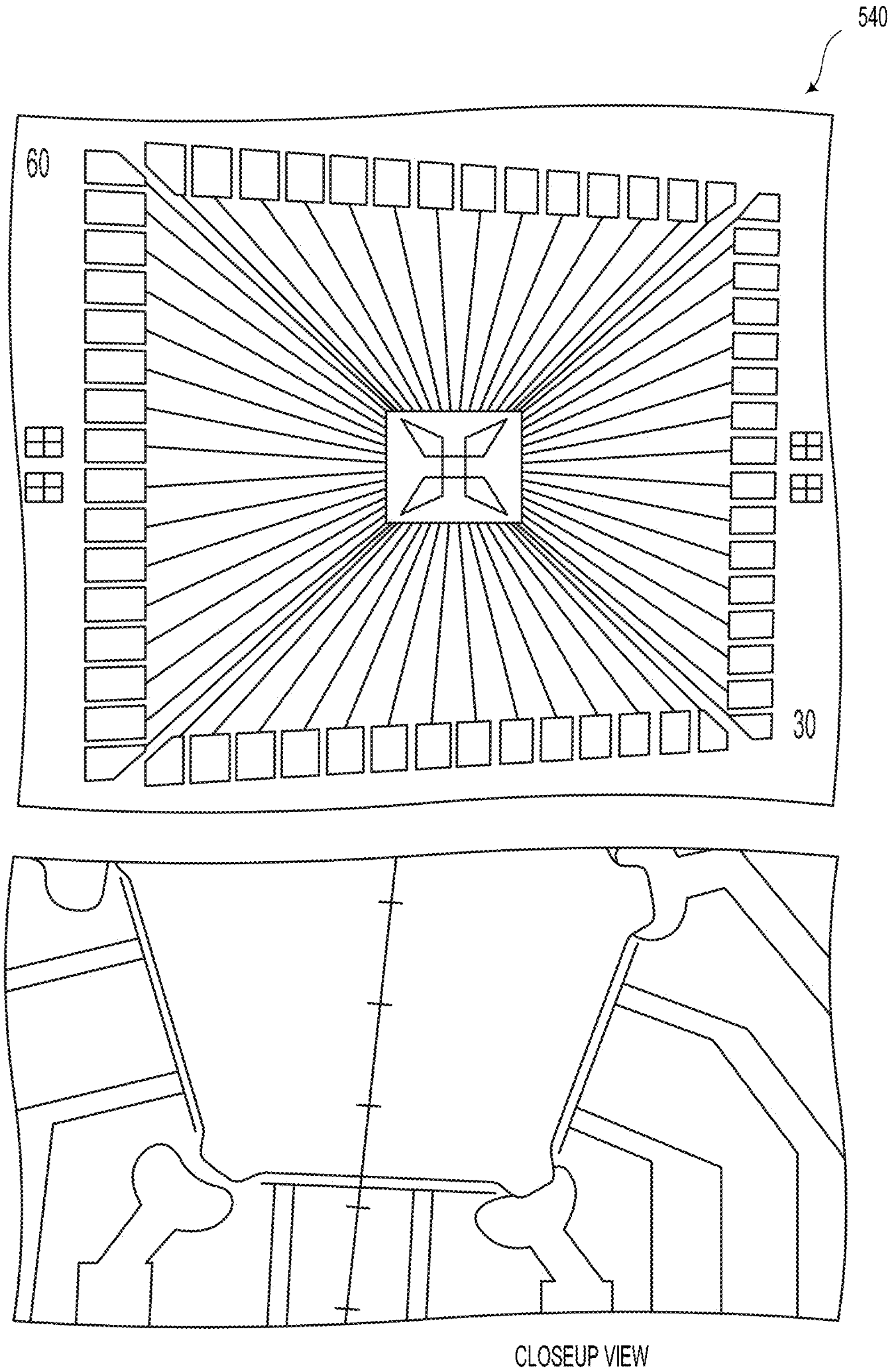
FIG. 5D is a schematic illustration of electrodes used for tube addressing and chimeric DNA guidance, according to an example embodiment.

FIG. 5D is a schematic illustration 540 of electrodes used for tube addressing and chimeric DNA guidance, according to an example embodiment. As shown in FIG. 5D, the S-RuM tube electrode array could be incorporated into a microfluidic system configured to accommodate DNA capture, hold, release, write, and read functions. Unlike conventional QB chip designs, DNA strands in the present microfluidic system will be guided to a nanopore read device. Furthermore, the DNA strands released from the S-RuM tubes will go through a denaturation and linearization process enabled by a built-in heater and a nanopillar array, which is depicted as a grid of pillar-like structures in FIG. 4. The nanopillar arrays could be fabricated using both reactive ion etching and/or metal-assisted chemical etching.

Figure 5E:
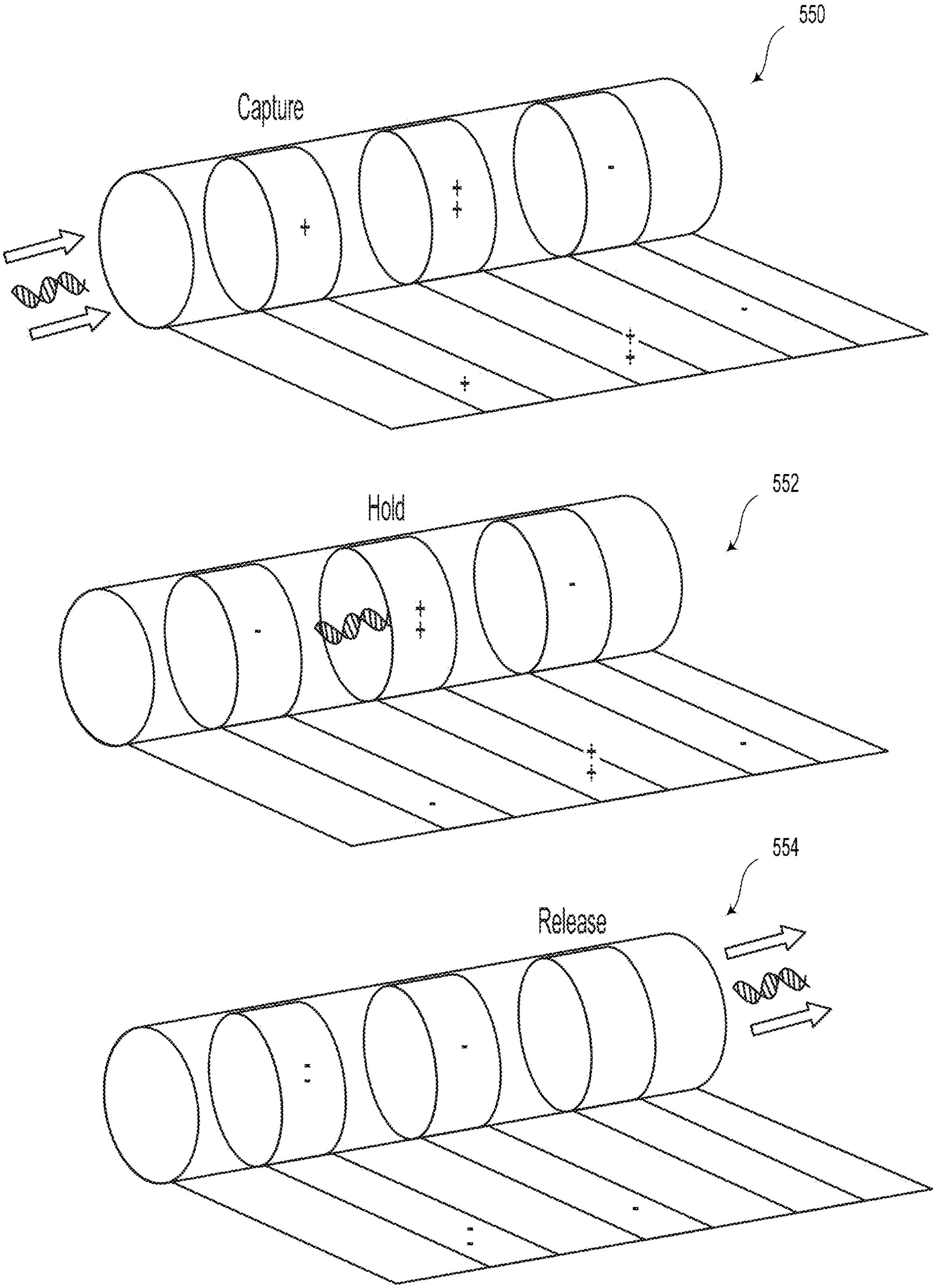
FIG. 5E illustrates capture, hold and release mechanisms for DNA according to an applied voltage on electrode pads, according to an example embodiment.

FIG. 5E illustrates capture mechanism 550, hold mechanism 552, and release mechanism 554 for DNA according to an applied voltage on respective electrode pads 562, according to an example embodiment. To guide specific chimeric DNA content into different selected tubes, a 3D cuff electrode system is disclosed based on using graphene as a conductor instead of Au. Sequentially placement into the tubes is regulated by setting the electrical bias to positive voltage through electrostatic attractive force, while leaving the rest of the tubes unbiased or negatively biased to prevent the DNAs from entering them. By varying the bias magnitude and polarity, the contents in a given tube can be released on demand to the desired extent, thereby controlling the concentration of the DNA substrate both within the tubes and in the integrated sample preparation system.

Through local stress and thickness control, the tube diameter may be engineered to vary along the axial as well as in the radial direction. In this way, conical, spiral, and multi-turns turn tubes with a defined gap between turns as small as a few nanometers may be realized. Such structures can be simulated through FEM and practically test which one of them is most suitable and stable as a chimeric DNA repository. More specifically, two approaches could be used to engineer the channel dimension in parallel: one approach is through thickness and stress control of the wall membrane to define the inner diameter of a single wall tube; another approach is through inducing or relieving local stress to define the gap between multi-turn tube while capping the central opening. This will allow for chimeric DNA to be pulled through either the inner diameter or through the gaps between turns and across each strip of graphene electrodes; multiple MLG strips enable redundancy checks as the DNA is pulled across the strips, which can be constructed by standard lithography. The microtube can be made to have any desired diameter using Parylene-C vapor backfilling to thicken the microtube walls and thus decrease the inner tube diameter if needed. Multiple microtubes will be used in parallel to improve throughput. In addition each microtube may be designed to contain a specific target that attracts certain types of molecules, each type of tube being transfer printed onto a common substrate to form the final device.

According to an example embodiment, DNA may be pulled into the microtube upon applying a positive bias on the first electrode, whereupon the DNA molecule is trapped within the microtube via electrostatic confinement via a negative bias on both electrodes. The DNA capture process 550 is illustrated in FIG. 5E. Individual microtubes may release DNA into the nanopillar array upon receiving a positive bias to the second electrode. The DNA release process 554 is illustrated in FIG. 5E. In some embodiments, the microtube could be biased so as to hold the DNA as illustrated in the hold process 552 of FIG. 5E.

Figure 5F:
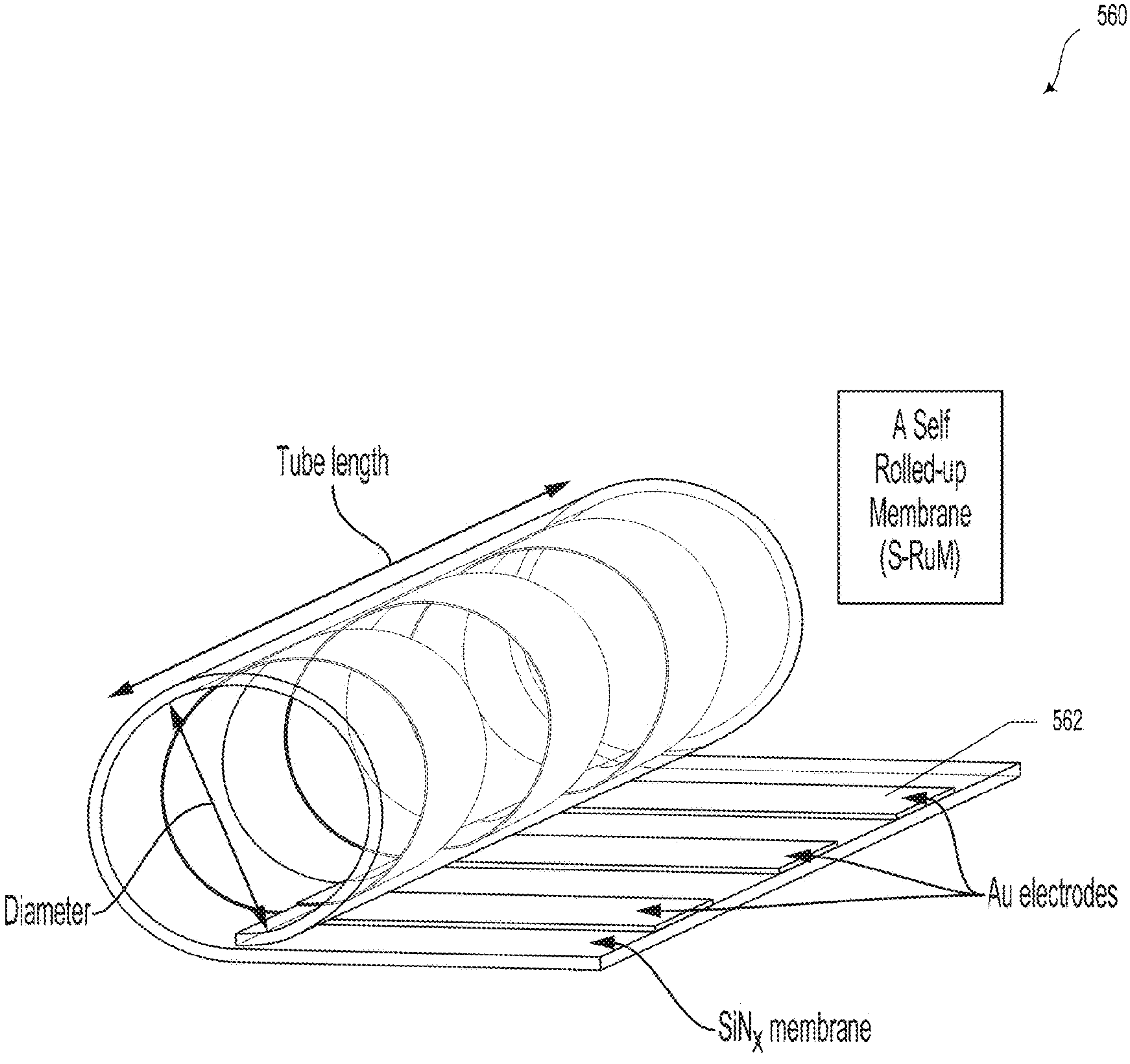
FIG. 5F is a schematic illustration of an S-RuM tube, according to an example embodiment.

FIG. 5F is a schematic illustration 560 of an S-RuM tube, according to an example embodiment.

Figure 5G:
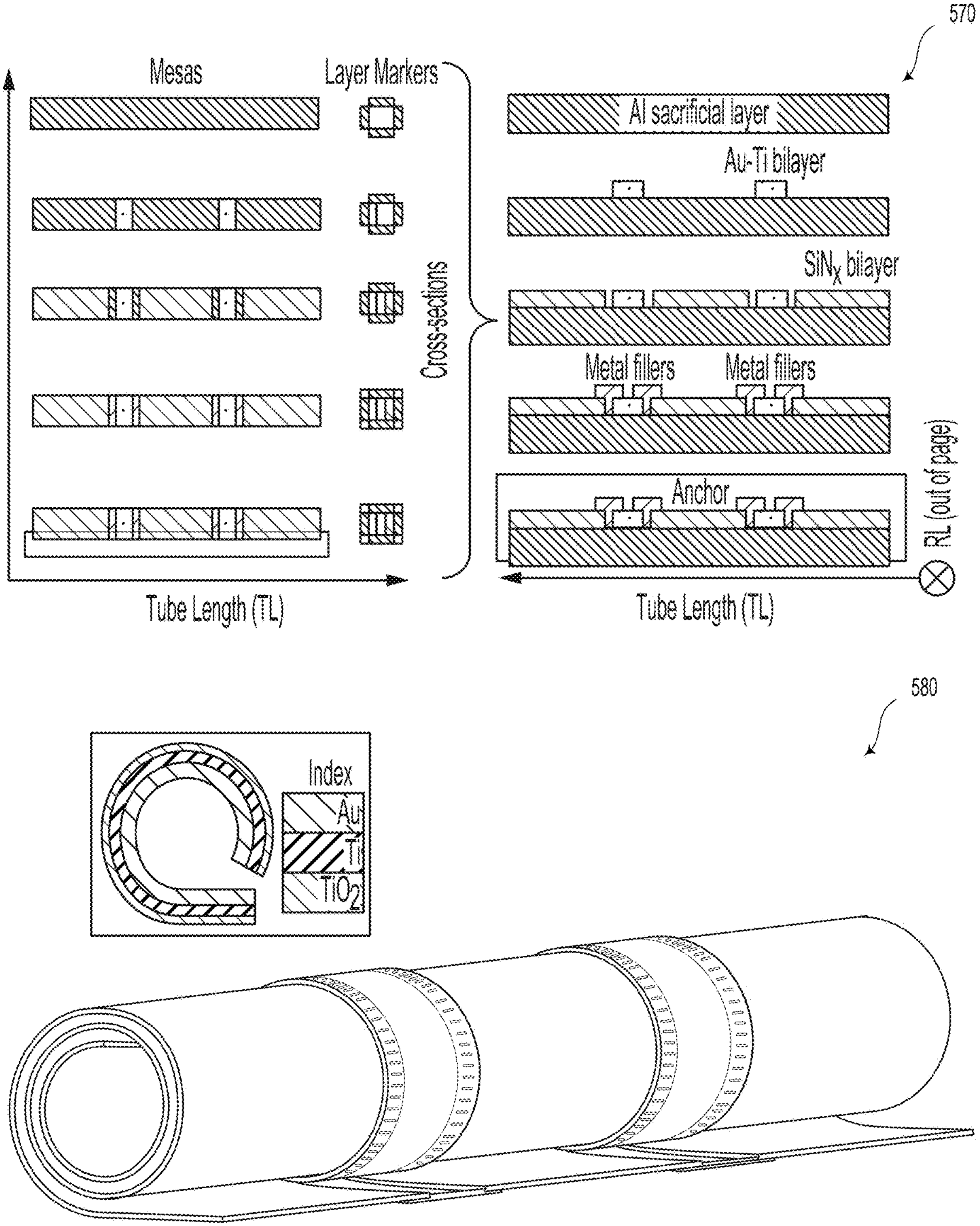
FIG. 5G is a schematic illustration of an S-RuM tube and a method for its manufacture, according to an example embodiment.

FIG. 5G is a schematic illustration of an S-RuM tube 580 and a method for its manufacture 570, according to an example embodiment. To implement the guide electrodes, patterned metal stripes may be added on top of the strained bilayer before rolling it so as to form 3D cuff electrodes inside the tube walls. Specifically, the implemented structure includes rolled up graphene electrodes on a plasma-enhanced chemical vapor deposition (PECVD) $SiN_x$ strained bilayer, sandwiched between several electrodes, both along the flow direction and perpendicular, normal to the substrate. Multilayer graphene (MLG) will be transferred onto the $SiN_x$ bilayer. Once the sacrificial layer is removed beneath the $SiN_x$ bilayer, the stack will roll into a microtubular shape, where the inner wall is lined with strips of graphene functioning as the electrodes. In some embodiments, the tube could be encased in a polydimethylsiloxane (PDMS) stamp containing channels running along the flow direction. Each electrode is addressed individually with desired polarity and bias. Local fields will be manipulated by rolled up, inner tube electrodes whereas global fields will be applied along the flow. Several electric fields along the flow direction will be applied to transfer chimeric DNA and control it in a dynamic and accurate fashion.

The method of fabricating the present array of microtubes could be performed in various ways. In some embodiments, the microtubes could be configured to selectively bias them for use in DNA storage applications. As a first approach, $SiN_X$ S-RuMs with three cuffed-in electrodes could be fabricated. In some embodiments, prior to rolling the microtube, three metal electrodes equidistant from each other could be patterned over the $SiN_x$ strained bilayer. The rolled-up membrane will have then three cuffed-in electrodes which could be used for guiding DNA into the tube, holding it, and then releasing it. These guide electrodes will be biased accordingly to perform the storage and release action.

Since DNA is a negatively charged molecule, a positive potential can be applied on the outer most cuffed-in electrode to drive the DNA inside the tube. A reverse higher negative voltage at the other outer most cuffed-in electrode could prevent the DNA from leaking out of the microtube. In some embodiments, the middle electrode can be biased positively (under holding operation) or negatively (under releasing operation).

The planar electrode approach is not as beneficial as compared to the 3D tubular approach because the electric field inside a cylinder can be more uniform and potentially more highly concentrated. The diameter of the $SiN_x$ tubes may be minimized so that sufficient field (field required to capture or release a DNA) can be generated within the tube without reaching the breakdown limits of the material. Single turn SiNx, without the electrodes, can have diameter as low as 2.7 μm. In some embodiments, the electrodes could include a metallic bilayer system including Au (tensile) and Ti (compressive) layers.

As a second approach, individually biased Au—Ti S-RuMs isolated by $SiN_x$ filler tubes could be formed by utilizing a Au—Ti strained bilayer system to form the microtubes. As the sacrificial layer is etched away, the bottom Ti layer gets oxidized in the process, providing excess momentum and driving force for rolling. Since the inside of the tube is still composed of Au and is thus conducting, each tube can then be individually biased for DNA capture, hold, and release actions. However, spacing between the tubes is limited by lithography and the DNA is thus subjected to potential leakage. In order to prevent the DNA from leaking out of the microtubes, the idea of $SiN_x$ filler tubes is proposed. In this approach, the $SiN_x$ bilayer system will be overlapped with a Au—Ti bilayer system to act as isolation tubes in between the conducting Au—Ti tubes. In some embodiments, the Au—Ti tubes may be biased similarly as the three cuffed-in electrodes in $SiN_x$ tube system. This system is yet to be optimized as both $SiN_x$ and Au—Ti bilayer systems operate based on different rolling mechanisms. In order to combine the rolling mechanics of $SiN_x$ and Au—Ti bilayer system, several test runs may be made to identify the optimum rolling conditions by adjusting etching and lithography parameters.

Even with the smaller diameters of 1.5 μm, Au—Ti tubes do not collapse under capillary forces and prove to be a more robust system for microfluidic applications. The ability to fabricate a Au—Ti array of tubes demonstrates that $SiN_x$ S-RuMs could be combined with Au—Ti S-RuMs with high yield and consistency. $SiN_x$ has a positive zeta potential (intrinsic positive charge) and thus will facilitate DNA capture. $TiO_2$ on the other hand is known to have a slight negative zeta potential, however, could be varied with change in pH and concentration of the electrolyte.

It will be understood that DNA-based data storage system 400 could include a controller that could be configured to control one or more of its operations. Such a controller could include, for instance, an instruction memory. The instruction memory could be configured to provide instructions configured to control or otherwise operate various elements of DNA-based data storage system 400. The instructions may be stored in a permanent or transitory manner in the instruction memory.

The controller could include, for example, a field-programmable gate array (FPGA) or an application-specific integrated circuit (ASIC). Other types of processors, circuits, computers, or electronic devices configured to carry out software instructions are contemplated herein. It will be understood that other ways to implement DNA-based data storage system 400 are possible and contemplated herein.

The DNA-based data storage system 400 could be implemented in a computing device, such as an external computer, or a mobile computing platform, such as a smartphone, tablet device, personal computer, wearable device, etc. Additionally or alternatively, the DNA-based data storage system 400 can include a computer, or could be connected to, a remotely-located computer system, such as a cloud server network. Furthermore, DNA-based data storage system 400 could include, or be incorporated into, a robotic system, an aerial vehicle, a smart home device, a smart infrastructure system, among other possibilities. Without limitation, the DNA-based data storage system 400 could additionally or alternatively include at least one deep neural network, another type of machine learning system, and/or an artificial intelligence system.

The memory devices described herein may include a non-transitory computer-readable medium, such as, but not limited to, read-only memory (ROM), programmable read-only memory (PROM), erasable programmable read-only memory (EPROM), electrically erasable programmable read-only memory (EEPROM), non-volatile random-access memory (e.g., flash memory), a solid state drive (SSD), a hard disk drive (HDD), a Compact Disc (CD), a Digital Video Disk (DVD), a digital tape, read/write (R/W) CDs, R/W DVDs, etc.

IV. Example Methods

Figure 6:
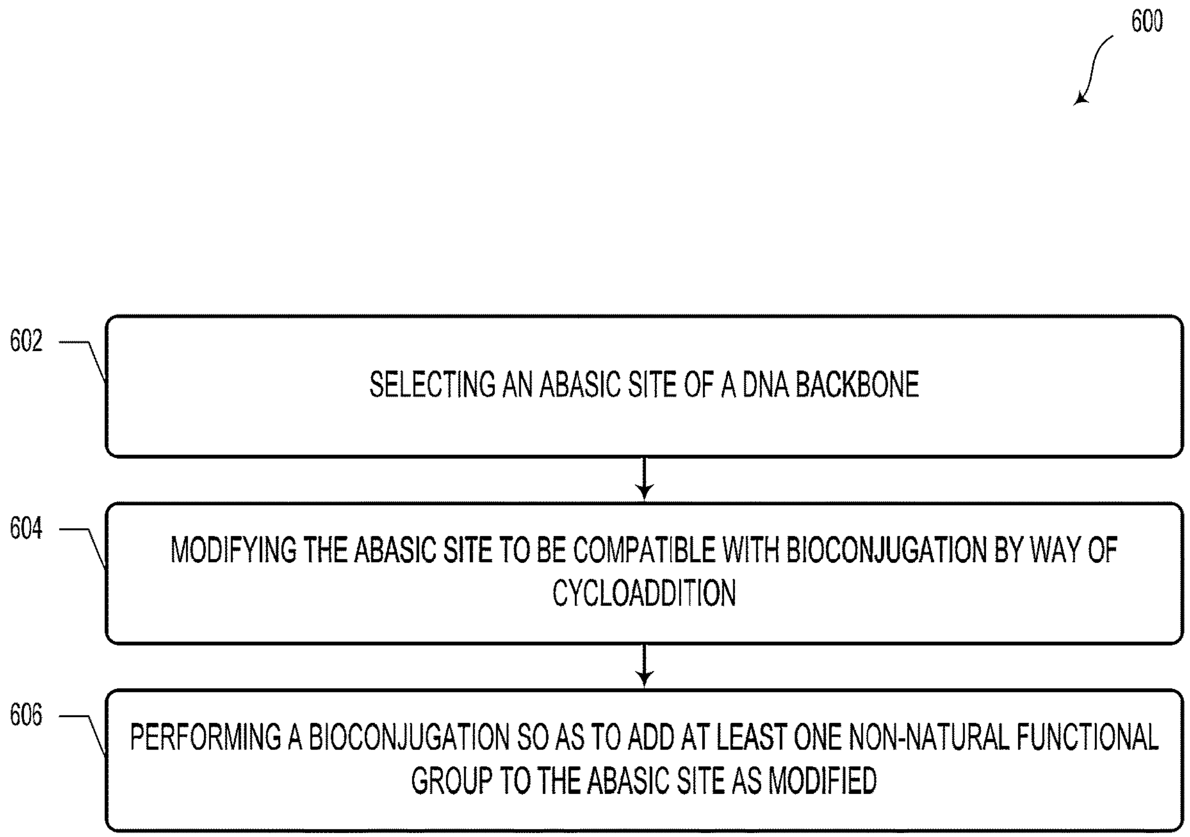
FIG. 6 illustrates a method, according to an example embodiment.

FIG. 6 illustrates a method 600, according to an example embodiment. It will be understood that the method 600 may include fewer or more steps or blocks than those expressly illustrated or otherwise disclosed herein. Furthermore, respective steps or blocks of method 600 may be performed in any order and each step or block may be performed one or more times. In some embodiments, some or all of the blocks or steps of method 600 may be carried out to form one or more DNA-based data storage elements (e.g., DNA-based data storage element 100). It will be understood that other scenarios are possible and contemplated within the context of the present disclosure.

Method 600 could include a way to synthesize a DNA-based data storage element.

Block 602 of method 600 could include selecting an abasic site of a DNA backbone.

Block 604 of method 600 could include modifying the abasic site to be compatible with bioconjugation by way of cycloaddition.

Block 606 of method 600 could include performing a bioconjugation so as to add at least one non-natural functional group to the abasic site as modified. In some embodiments, the modifying and bioconjugation steps could be carried out in a sequential, repeating manner so as to encode a predetermined sequence or arrangement of information.

In some embodiments, the bioconjugation could include an azide-alkyne Huisgen-type cycloaddition. Other types of bioconjugation are possible and contemplated.

In various examples, modifying the abasic site could be performed so as to form a bioconjugation click chemistry target.

In example embodiments, performing the bioconjugation could include adding at least one peptide nucleic acid (PNA). In such scenarios, the PNA could include a peptide backbone and a plurality of natural nucleobase monomers.

Figure 7:
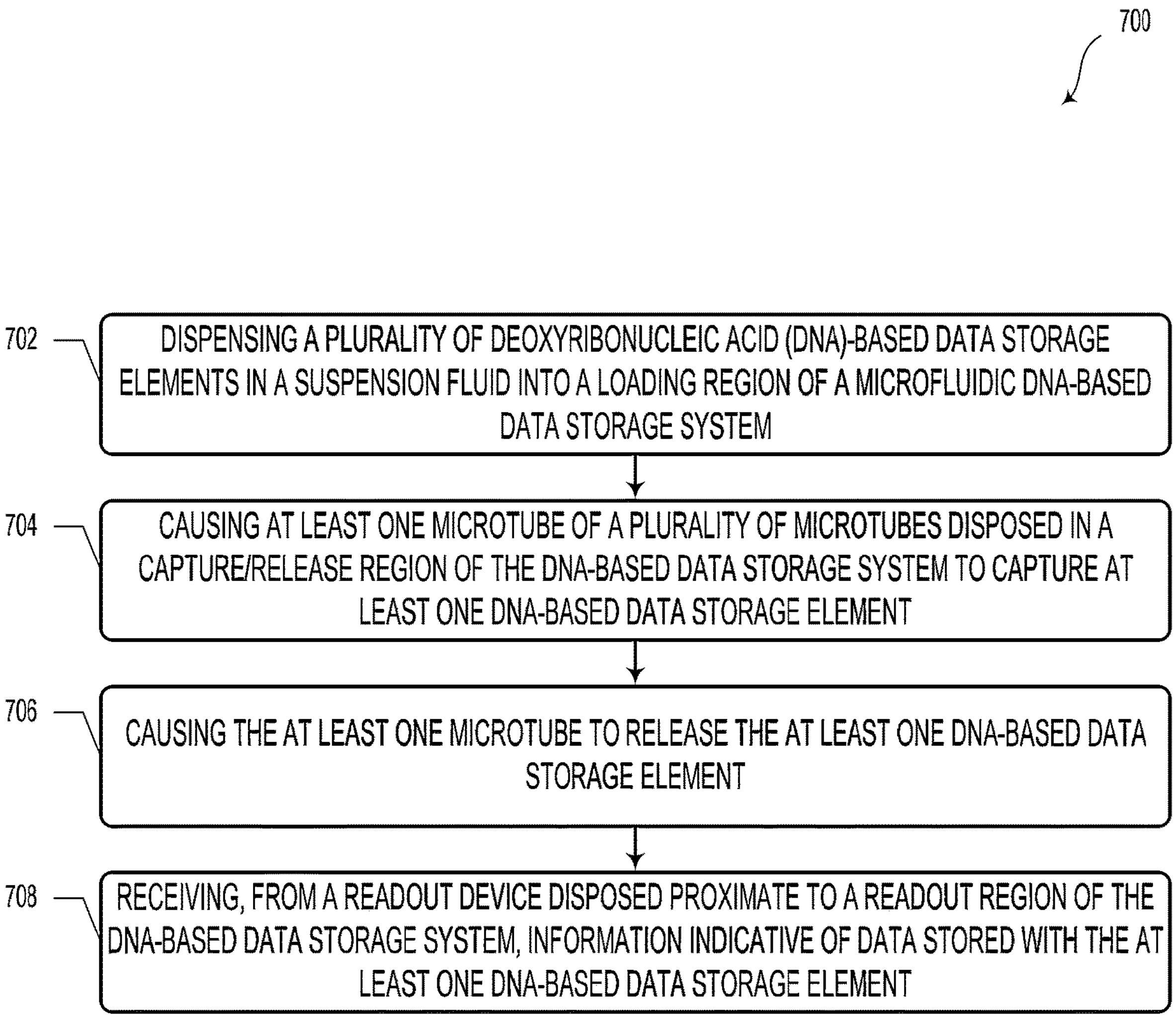
FIG. 7 illustrates a method, according to an example embodiment.

FIG. 7 illustrates a method 700, according to an example embodiment. It will be understood that the method 700 may include fewer or more steps or blocks than those expressly illustrated or otherwise disclosed herein. Furthermore, respective steps or blocks of method 700 may be performed in any order and each step or block may be performed one or more times. In some embodiments, some or all of the blocks or steps of method 700 may be carried out in the course of operating a DNA-based data storage system (e.g., DNA-based data storage system 400). For example, some or all of method 700 could be carried out so as to read, write, and/or store DNA-based data storage elements (e.g., DNA-based data storage element 100). It will be understood that other scenarios are possible and contemplated within the context of the present disclosure.

Block 702 of method 700 includes dispensing a plurality of deoxyribonucleic acid (DNA)-based data storage elements in a suspension fluid into a loading region of a microfluidic DNA-based data storage system.

Block 704 includes causing at least one microtube of a plurality of microtubes disposed in a capture/release region of the DNA-based data storage system to capture at least one DNA-based data storage element.

Block 706 includes causing the at least one microtube to release the at least one DNA-based data storage element.

Block 708 includes receiving, from a readout device disposed proximate to a readout region of the DNA-based data storage system, information indicative of data stored with the at least one DNA-based data storage element.

In some embodiments, causing the at least one microtube to capture or release the at least one DNA-based data storage element could include biasing a plurality of electrodes of the at least one microtube so as to capture or release the at least one DNA-based data storage element, respectively.

In various examples, method 700 could further include causing the at least one microtube to hold the at least one DNA-based data storage element within the at least one microtube.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, a physical computer (e.g., a field programmable gate array (FPGA) or application-specific integrated circuit (ASIC)), or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A method comprising:

dispensing a plurality of deoxyribonucleic acid (DNA)-based data storage elements in a suspension fluid into a loading region of a microfluidic DNA-based data storage system;

causing at least one microtube of a plurality of microtubes disposed in a capture/release region of the DNA-based data storage system to capture at least one DNA-based data storage element;

causing the at least one microtube to release the at least one DNA-based data storage element; and receiving, from a readout device disposed proximate to a readout region of the DNA-based data storage system, information indicative of data stored with the at least one DNA-based data storage element.

2. The method of claim 1, wherein causing the at least one microtube to capture or release the at least one DNA-based data storage element comprises biasing a plurality of electrodes of the at least one microtube so as to capture or release the at least one DNA-based data storage element, respectively.

3. The method of claim 1, further comprising causing the at least one microtube to hold the at least one DNA-based data storage element within the at least one microtube.

4. The method of claim 1, wherein the microtubes comprise bio-compatible self-rolled-up membranes.

5. The method of claim 1, wherein the microtubes comprise silicon nitride.

6. The method of claim 1, further comprising linearizing the DNA-based data storage element.

7. The method of claim 1, wherein the information indicative of data stored with the at least one DNA-based data storage element includes the detection of structural changes in DNA nucleotides.

* * * * *